United States Patent

Miyazawa et al.

[11] Patent Number: 5,578,603
[45] Date of Patent: Nov. 26, 1996

[54] AMINOBENZOIC ACID DERIVATIVES

[75] Inventors: Shuhei Miyazawa; Shigeki Hibi; Hiroyuki Yoshimura; Takashi Mori; Yorihisa Hoshino; Mitsuo Nagai; Kouichi Kikuchi; Hisashi Shibata; Kazuo Hirota; Takashi Yamanaka; Isao Yamatsu; Masanori Mizuno, all of Ibaraki, Japan

[73] Assignee: Eisai Co., Ltd., Tokyo, Japan

[21] Appl. No.: 337,480

[22] Filed: Nov. 8, 1994

Related U.S. Application Data

[62] Division of Ser. No. 13,080, Feb. 3, 1993, Pat. No. 5,389,643.

[30] Foreign Application Priority Data

Feb. 4, 1992 [JP] Japan .................................. 4-18959
Sep. 3, 1992 [JP] Japan .................................. 4-235533

[51] Int. Cl.$^6$ ........................ A61K 31/46; C07D 405/10
[52] U.S. Cl. ........................................... 514/304; 546/125
[58] Field of Search ............................. 546/125; 514/304

[56] References Cited

FOREIGN PATENT DOCUMENTS

| | | |
|---|---|---|
| 081054 | 6/1983 | European Pat. Off. . |
| 220011 | 4/1987 | European Pat. Off. . |
| 302699 | 2/1989 | European Pat. Off. . |
| 088364 | 6/1982 | United Kingdom . |

*Primary Examiner*—Alan L. Rotman
*Attorney, Agent, or Firm*—Birch, Stewart, Kolasch & Birch, LLP

[57] ABSTRACT

An aminobenzoic acid derivative represented by the following formulas (I-2) or (I-3), or a pharmacologically acceptable salt thereof, which exhibits a serotonin antagonism and an acetylcholine release accelerating activity at a well-balanced activity ratio and which is efficacious as a drug for patients with gastrointestinal unindentified complaints:

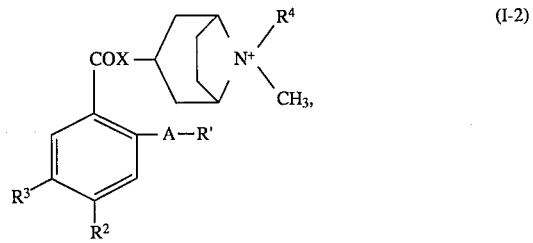

(I-2)

and

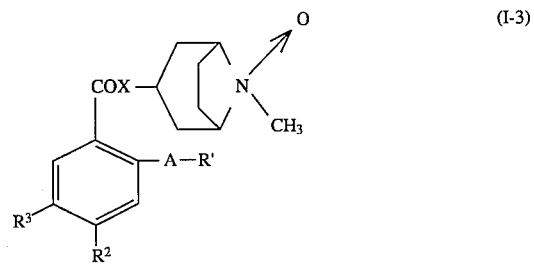

(I-3)

wherein $R^1$ represents a group such as an alkynyl or cyanoalkyl group; $R^2$ represents a group such as an amino or acylamino group; $R^3$ represents a halogen atom; X represents —O— or —N—; and A represents an oxygen or sulfur atom.

12 Claims, No Drawings

AMINOBENZOIC ACID DERIVATIVES

This application is a divisional of application Ser. No. 08/013,080, filed on Feb. 3, 1993, U.S. Pat. No. 5,389,643, the entire contents of which are hereby incorporated by reference.

BACKGROUND OF THE INVENTION

1. Field of the Invention

The present invention relates to an aminobenzoic acid derivative, particularly an aminobenzoic acid derivative useful as drugs, and a process for preparing the same.

2. Description of the Related Art

The proportion of patients with unidentified complaints such as abdominal full-consciousness, heartburn, nausea and vomiting among those with gastrointestinal diseases has recently increased steadily and now reaches 60% or above.

Most of these unidentified complaints are caused by functional abnormality of digestive tract. For example, it is known that a patient with epigastric unidentified complaints such as chronic gastritis is in a state of delayed gastric emptying, while a patient with hypogastric unidentified complaints such as irritable bowel syndrome including abnormal evacuation and abdominal pain as main symptoms is in a state of intestinal hyperanakinezia.

It is ascertained that stress and anxiety are causative of any unidentified complaint, and in this sense, it is not too much to say that unidentified complaint is one of modern diseases.

Dopamine antagonists, musculotropic agents for regulating the movement of smooth muscles and acetylcholine release accelerators are now used in order to ameliorate the above gastrointestinal unidentified complaints. However, dopamine antagonists cause potent adverse reactions such as parkinsonism, so that they must be used carefully; musculotropic agents for regulating the movement of smooth muscles cause adverse reactions such as constipation unfavorably; and acetylcholine release accelerators do not effectively act as an antiemetic or ataractic, thus being unsatisfactory.

Under these circumstances, the present inventors have set about making studies for the purpose of developing a drug which is efficacious in treating all types of patients with gastrointestinal unindentified complaints or gastrointestinal indefinite complaints without causing any potent adverse reaction and exhibits a depressant activity against anxiety which is nearly always found as one of the background factors of such patients.

As a result of the studies, it has been concluded that the above requirements can be fulfilled by a drug exhibiting both a serotonin (hereinafter abbreviated to "5HT$_3$") antagonism and an acetylcholine (hereinafter abbreviated to "ACh") release accelerating activity. Therefore, further studies have been made in order to find a compound exhibiting both the activities at a well-balanced activity ratio to find out that the object can be attained by using an aminobenzoic acid derivative represented by the following general formula (I) or a pharmacologically acceptable salt thereof. The present invention has been accomplished on the basis of this finding.

Although aminobenzoic acid derivatives useful as drugs have been described in Great Britain Patent Publication-A Nos. 1593146/1981 (BEECHAM GROUP LTD., Published on Jul. 15, 1981), 2125398/1984 (DONATSCH P; SANDOZ AG; SANDOZ-PATENT-GMBH; and SANDOZ SA, Published on Mar. 7, 1984) and 2205095/1988 (BRISTOL-MYERS SQIBB CO. and BRISTOL-MYERS CO., Published on Nov. 30, 1988), U.S. Pat. Nos. 4,797,406/1985 (SANDOZ-PATENT-GMBH; and SANDOZ SA, Published on Apr. 24, 1985) and 5,001,133/1991 (SANDOZ AG, Published on Mar. 19, 1991), European Patent Publication-A Nos. 189002/1986 (SANDOZ AG, Published on Jul. 30, 1986), 220011/1987 (BEECHAM GROUP PLC., Published on Apr. 29, 1987) and 302699/1989 (FORDONAL SA and WALTON SA, published on Feb. 8, 1989) and Great Britain Patent Publication-B No. 2169292/1988 (SANDOZ LTD., Published on Sep. 21, 1988), the compounds of the present invention are different from them in the chemical structures.

CONSTRUCTION OF THE INVENTION

Summary of the Invention

The compound of the present invention is an aminobenzoic acid derivative represented by the following general formulas (I), (I-2) or (I-3), or a pharmacologically acceptable salt thereof:

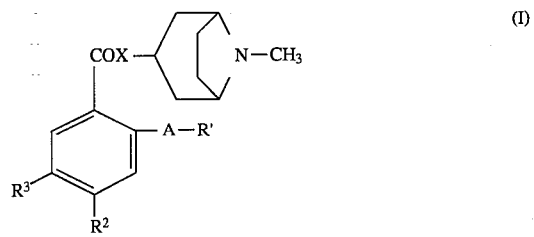

wherein $R^1$ represents a cyanoalkyl, cyanoalkenyl, substituted cycloalkyl, substituted or unsubstituted cycloalkylalkyl, halogen-substituted lower alkyl, alkenyl, alkynyl, saturated or unsaturated heterocyclicalkyl or saturated or unsaturated heterocyclic group;

$R^2$ represents an amino, acylamino, carboxyamino or alkylamino group;

$R^3$ represents a halogen atom;

X represents a group represented by the formulas: —O— or —NH—; and

A represents an oxygen or sulfur atom, with the proviso that when $R^1$ represents a saturated or unsaturated heterocyclic group, the saturated or unsaturated heterocyclic group is one exclusive of tetrahydrofuranyl and 1,3-benzodioxolanyl, that when $R^1$ represents a saturated or unsaturated heterocyclicalkyl group, the saturated or unsaturated heterocyclic group constituting the saturated or unsaturated heterocyclicalkyl group is one exclusive of tetrahydrofuranyl and 1,3-benzodioxolanyl, that when A represents an oxygen atom and $R^1$ represents a halogen-substituted lower alkyl group, the group represented by the formula: —A—$R^1$ is a group exclusive of one represented by the formula: —O—(CH$_2$)$_r$—CF$_3$ (wherein r is 0 or an integer of 1 to 4) and that when $R^1$ represents an unsubstituted cycloalkylalkyl group, the unsubstituted cycloalkylalkyl group is one exclusive of one represented by the formula: —(CH$_2$)$_m$—R (wherein R is a cycloalkyl group and m is an integer of 1 to 6);

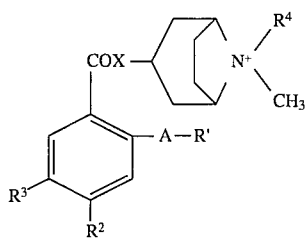

(I-2)

wherein

R¹ represents a cyanoalkyl, cyanoalkenyl, substituted cycloalkyl, substituted or unsubstituted cycloalkylalkyl, halogen-substituted lower alkyl, alkenyl, alkynyl, saturated or unsaturated heterocyclicalkyl or saturated or unsaturated heterocyclic group;

R² represents an amino, acylamino, carboxyamino or alkylamino group;

R³ represents a halogen atom;

X represents a group represented by the formulas: —O— or —NH—;

A represents an oxygen or sulfur atom; and

R⁴ represents a lower alkyl or aralkyl group, and

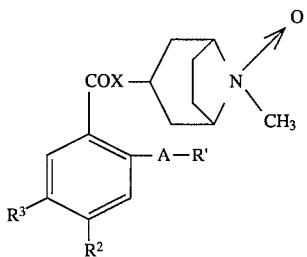

(I-3)

wherein

R¹ represents a cyanoalkyl, cyanoalkenyl, substituted cycloalkyl, substituted or unsubstituted cycloalkylalkyl, halogen-substituted lower alkyl, alkenyl, alkynyl, saturated on unsaturated heterocyclicalkyl or saturated or unsaturated heterocyclic group;

R² represents an amino, acylamino, carboxyamino or alkylamino group;

R³ represents a halogen atom;

X represents a group represented by the formulas: —O— or —NH—; and

A represents an oxygen or sulfur atom.

Specific examples of the aminobenzoic acid derivative according to the present invention include;

(1) compounds represented by the general formulas (I), (I-2) and (I-3), with the proviso that R¹ is an alkynyl group;

(2) compounds represented by the general formulas (I), (I-2) and (I-3), with the proviso that R² is an amino group;

(3) compounds represented by the general formula (I), with the proviso that R¹ in the general formula (I) represents a cyanoalkyl, cyanoalkenyl, substituted cycloalkyl, substituted cycloalkylalkyl, halogen-substituted lower alkyl, alkenyl, alkynyl, saturated or unsaturated heterocyclicalkyl or saturated or unsaturated heterocyclic group or a group represented by the formula: —CH(CH₃)R' (wherein R' is a cyclopentyl group);

(4) compounds represented by the following general formula (II):

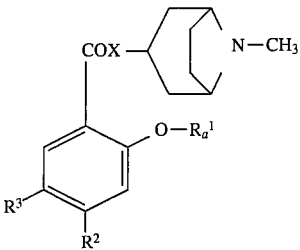

(II)

wherein

R¹ₐ represents an alkynyl group;

R² represents an amino, acylamino, carboxyamino or alkylamino group;

R³ represents a halogen atom; and

X represents a group represented by the formulas: —O— or —NH—;

(5) compounds represented by the general formulas (I-2) and (I-3); and (6) the compound represented by the following formula (I-3-1):

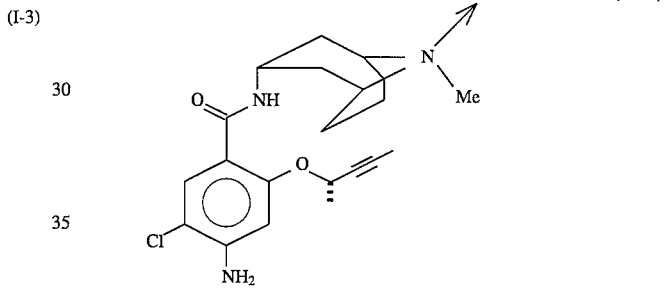

(I-3-1)

Specific examples of the pharmacologically acceptable salt of the aminobenzoic acid derivative according to the present invention include;

(1) pharmacologically acceptable salt of the compounds (1) to (6) described above as specific examples of the aminobenzoic acid derivative according to the present invention, and (2) the compound represented by the following formula (I-2-1):

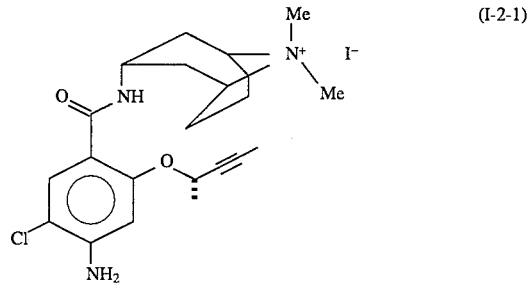

(I-2-1)

The present invention also relates to a preventive and therapeutic agent for diseases for which serotonin antagonism or an acetylcholine release accelerating activity is efficacious, which comprises the aminobenzoic acid derivative or the pharmacologically acceptable salt thereof according to the present invention as an active ingredient.

Further, the present invention relates agents such as an agent for raising a gastrointestinal function; e.g., a gastric emptying function, an antiemetic, an ataractic, a preventive and therapeutic agent for irritable bowel syndrome, a preventive and therapeutic agent for amnestic syndrome, senile dementia, Alzheimer disease or dependence, which comprise the aminobenzoic acid derivative or the pharmacologically acceptable salt thereof according to the present invention as an active ingredient.

The present invention relates a pharmacological composition which comprises a therapeutically effective amount of the aminobenzoic acid derivative or the pharmacologically acceptable salt thereof according to the present invention and a pharmacologically acceptable vehicle.

Furthermore, the present invention relates a use of the aminobenzoic acid derivative or the pharmacologically acceptable salt thereof according to the present invention for the making of a medicament for treating a disease for which serotonin antagonism or an acetylcholine release accelerating activity is efficacious.

The present invention relates a method for treating a disease which comprises administering a pharmaceutically effective amount of the aminobenzoic acid derivative or the pharmacologically acceptable salt thereof according to the present invention to a patient suffering from a disease for which serotonin antagonism or an acetylcholine release accelerating activity is efficacious.

The present invention also relates an aminobenzoic acid derivative represented by the following general formula (a) or a pharmacologically acceptable salt thereof:

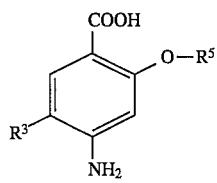
(a)

wherein $R^3$ represents a halogen atom and $R^5$ represents a lower alkynyl group having 3 to 10 carbon atoms which may be substituted.

Further, the present invention relates a process for producing the aminobenzoic acid derivative represented by the above general formula (a) or the pharmacologically acceptable salt thereof, which comprises reacting a 4-amino-5-halogen-salicylic acid derivative, wherein the amino group and the calboxylic group are protected with protective groups which are inactive to an organic synthesis, with an alkynol in the presence of triphenylphosphine and dialkylazocarboxylate, followed by deprotecting the protective groups.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In the general formulas (I), (I-2) and (I-3), the lower alkyl group constituting the halogen-substituted lower alkyl group as defined with respect to $R^1$ is a straight-chain or branched alkyl group having 1 to 8 carbon atoms and examples thereof include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 3-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl and octyl groups. Further, the halogen atom constituting the halogen-substituted lower alkyl group includes fluorine, chlorine, bromine and iodine atoms and the number of the substituting halogen atoms is preferably 1 to 3. Furthermore, the halogen atom may be bonded to any of the carbon atoms constituting the lower alkyl group, with the proviso that when the aminobenzoic acid derivative is selected from the compounds consisting of those represented by the general formula (I), a case wherein the group represented by the formula: $-A-R^1$ in the formula (I) is a group represented by the formula: $-O-(CH_2)_r-CF_3$ (wherein r is 0 or an integer of 1 to 4) is excepted.

The alkyl group constituting the cyanoalkyl group as defined with respect to $R^1$ is a lower alkyl group as described in the definition of the halogen-substituted lower alkyl group (hereinafter abbreviated to "the above-defined lower alkyl group"). The cyano group may be bonded to any of the carbon atoms constituting the alkyl group and the alkyl group is preferably substituted by 1 or 2 cyano groups.

The alkenyl group as defined with respect to $R^1$ is one derived from the above-defined lower alkyl group in which one or more carbon-carbon single bonds are replaced by carbon-carbon double bonds, though the double bonds may be present at arbitrary positions.

The alkynyl group as defined with respect to $R^1$ is one derived from the above-defined lower alkyl group in which one or more carbon-carbon single bonds are replaced by triple bonds, though the triple bonds may be present at arbitrary positions. Examples of the alkynyl group are as follows, though the alkynyl groups according to the present invention is not limited to them:

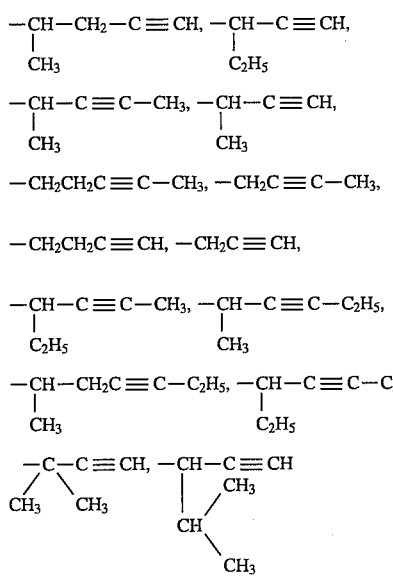

Particularly preferable examples thereof include groups represented by the formulas:

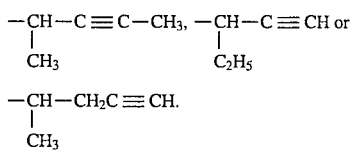

The cyanoalkenyl group as defined with respect to $R^1$ is an alkenyl group as defined above which is substituted by one or two cyano groups at arbitrary positions.

The cycloalkyl group constituting the substituted cycloalkyl group as defined with respect to $R^1$ is one having 3 to 8 carbon atoms, preferably 5 or 6 carbon atoms. Preferable examples of the substituent include lower alkyl, lower alkoxy, carboxyl, cyano and amino groups.

The cylcoalkyl group constituting the substituted or unsubstituted cycloalkylalkyl group as defined with respect to $R^1$ is the cycloalkyl group as described above. Further, the substituent of the substituted cycloalkylalkyl group is a group as defined with respect to the substituent of the above-defined substituted cycloalkyl group.

The alkyl group constituting the substituted or unsubstituted cycloalkylalkyl group as defined with respect to $R^1$ is the above-defined lower alkyl group. The substituted or unsubstituted cycloalkyl group may be bonded to any of the carbon atoms constituting the alkyl group and the alkyl group is preferably substituted by one substituted or unsubstituted cycloalkyl group.

When $R^1$ represents an unsubstituted cycloalkylalkyl group, the alkyl group is preferably a branched alkyl group. Further, when the aminobenzoic acid derivative is selected from the compounds consisting of those represented by the general formula (I) and when $R^1$ represents an unsubstituted cycloalkylalkyl group, the unsubstituted cycloalkylalkyl group is one exclusive of one represented by the formula: $-(CH_2)_m-R$ (wherein R is a cycloalkyl group and m is an integer of 1 to 6).

The saturated or unsaturated heterocyclic group as defined with respect to $R^1$ is a saturated or unsaturated 5- to 7-membered ring group having one or two oxygen, nitrogen and/or sulfur atoms. When the aminobenzoic acid derivative is selected from the compounds consisting of those represented by the general formula (I), the saturated or unsaturated heterocyclic group is a group exclusive of tetrahydrofuranyl and 1,3-benzodioxolanyl.

The saturated or unsaturated heterocyclic group constituting the saturated or unsaturated heterocyclicalkyl group as defined with respect to $R^1$ is a heterocyclic group as described above in the definition of the saturated or unsaturated heterocyclic group. When the aminobenzoic acid derivative is selected from the compounds consisting of those represented by the general formula (I), the saturated or unsaturated heterocyclic group constituting the saturated or unsaturated heterocyclicalkyl group is a group exclusive of tetrahydrofuranyl and 1,3-benzodioxolanyl.

The alkyl group of the saturated or unsaturated heterocyclicalkyl group is the above-defined lower alkyl group. The saturated or unsaturated heterocyclic group may be bonded to any of the carbon atoms constituting the alkyl group and the alkyl group is preferably substituted by one saturated or unsaturated heterocyclic group.

The acyl group constituting the acylamino group as defined with respect to $R^2$ may be one derived from any carboxylic acid selected from among aliphatic saturated carboxylic acids, aliphatic unsaturated carboxylic acids, saturated and unsaturated carbocyclic carboxylic acids, heterocyclic carboxylic acids, hydroxy carboxylic acids, and alkoxy carboxylic acids, and examples of the acyl group include lower alkanoyl groups such as formyl, acetyl, propionyl, butyryl, valeryl, isovaleryl and pivaloyl groups; aroyl groups such as benzoyl, toluoyl and naphthoyl groups; and heteroaroyl groups such as furoyl, nicotinoyl and isonicotinoyl groups.

The acylamino group may be either a monosubstituted [—NH-(acyl group)] or disubstituted one

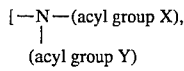

wherein the acyl groups X and Y may be same or different from each other], the former being preferable.

The carboxyamino group as defined with respect to $R^2$ is a group represented by the formula: —NH—COOH.

The alkyl group constituting the alkylamino group as defined with respect to $R^2$ is the above-defined lower alkyl group. The alkylamino group may be either a monosubstituted [—NH-(alkyl group)] or disubstituted one

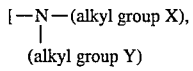

wherein the acyl groups X and Y may be same or different from each other], the former being preferable.

The halogen atom as defined with respect to $R^3$ includes fluorine, chlorine, bromine and iodine atoms, among which chlorine atom is preferable.

The lower alkyl group as defined with respect to $R^4$ is the above-defined lower alkyl group as defined with respect to $R^1$.

The alkyl group constituting the aralkyl group as defined with respect to $R^4$ is the above-defined lower alkyl group as defined with respect to $R^1$. The aralkyl group as defined with respect to $R^4$ is one wherein a hydrogen atom of the lower alkyl group constituting the aralkyl group is substituted by an aryl group.

The lower alkynyl group having 3 to 10 carbon atoms as defined with respect to $R^5$ is the alkynyl group as defined with respect to $R^1$, with the proviso that the number of carbon atoms is 3 to 10.

The lower alkynyl group having 3 to 10 carbon atoms defined with respect to $R^5$ of the general formula (a) includes propargyl, 1-propyn-1-yl, 1-butyn-1-yl, 2-butyn-1-yl, 3-butyn-1-yl, 3-butyn-2-yl, 1-pentyn-1-yl, 1-pentyn-3-yl, 1-pentyn-4-yl, 2-pentyn-1-yl, 3-pentyn-1-yl, 3-pentyn-2-yl, 4-pentyn-1-yl, 3-methyl-1-butyn-1-yl, 2-methyl-3-butyn-1-yl, 3-methyl-1-butyn-3-yl, 1-hexyn-1-yl, 1-hexyn-3-yl, 1-hexyn-4-yl, 1-hexyn-5-yl, 2-hexyn-1-yl, 2-hexyn-4-yl, 2-hexyn-5-yl, 3-hexyn-1-yl, 3-hexyn-2-yl, 4-hexyn-1-yl, 5-hexyn-1-yl, 1-methyl-3-pentyn-2-yl, 3, 3-dimethyl-1-butyn-1-yl, 2, 2-dimethyl-3-butyn-1-yl, 4-heptyn-1-yl, 4-heptyn-2-yl and 4-heptyn-3-yl groups. When $R^4$ has a substituent, the substituent is, for example, a lower alkyl, lower cycroalkyl, lower alkenyl, lower halogenated alkyl, lower alkoxy, cyano, lower cyanoalkyl, aryl or arylalkyl group or a halogen atom.

The pharmacologically acceptable salt according to the present invention includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate.

Further, the aminobenzoic acid derivative of the present invention may form a metal salt such as sodium, potassium, calcium or magnesium salt or may be present as a hydrate. The pharmacologically acceptable salt of the present invention include these metal salts and hydrates.

Although the compound of the present invention may be present as geometrical isomers or optical isomers, it is needless to say that the present invention includes all of the isomers.

Preferable groups of the compounds according to the present invention will now be described. The most desirable group of the compounds are those represented by the following general formula (II):

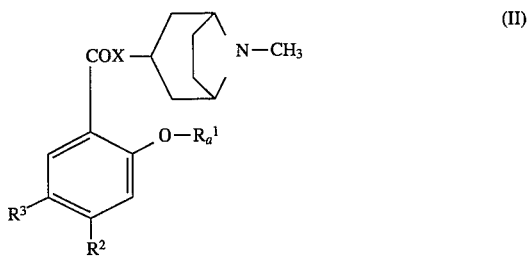

wherein $R^1_a$ represents an alkynyl group; and X, $R^2$ and $R^3$ are each as defined above.

X is particularly preferably a group represented by the formula: —NH—. $R^2$ is particularly preferably an amino or acylamino group. $R^3$ is particularly preferably a chlorine atom.

Particularly preferable examples of the alkynyl group as defined with respect to $R^1_a$ are as follows:

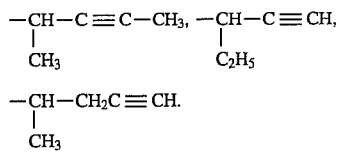

The compounds according to the present invention exhibit a scrotonin antagonism and an acetylcholine release accelerating activity. The serotonin antagonism means a $5\text{-}HT_3$ antagonism.

The especially preferred compound of the present invention is (−)-endo-4-amino-5-chloro-N-(8-methyl-8-azabicyclo[3.2.1]oct-3-yl)-2-{(3-pentyn-2-yl)oxy}benzamide hydrochloride.

The compounds represented by the general formulas (I), (I-2) and (I-3) can be produced from aminobenzoic acid derivatives represented by the general formula (a) or pharmacologically acceptable salts thereof.

The compound represented by the general formula (a) is the intermediate of the compound represented by the general formulas (I), (I-2) or (I-3). That is, the compound represented by the general formula (a) is useful as the starting material for synthesizing the compound represented by the general formulas (I), (I-2) or (I-3).

The compounds represented by the general formula (a) are novel compounds.

Particularly preferred compounds of the general formula (a) are the following compounds and pharmacologically acceptable salts thereof:
4-amino-5-chloro-2-{(3-pentyn-2-yl)oxy}benzoic acid,
4-amino-5-chloro-2-{(1-pentyn-4-yl)oxy}benzoic acid,
4-amino-5-chloro-2-{(1-pentyn-3-yl)oxy}benzoic acid,
4-amino-5-chloro-2-{(3-butyn-2-yl)oxy}benzoic acid,
4-amino-5-chloro-2-{(2-hexyn-4-yl)oxy}benzoic acid, and
4-amino-5-chloro-2-{(1-hexyn-3-yl)oxy}benzoic acid.

Although the compound represented by the general formula (a) may be present as geometrical isomers or optical isomers, it is needless to say that the present invention includes all of the isomers. When a final product represented by the general formulas (I), (I-2) or (I-3) is an optically active substance, an optically active substance represented by the general formula (a) may be employed as the starting material, or, alternatively, a racemic modification represented by the general formula (a) may be employed as the starting material and optical resolution may be conducted in any step of the synthesis process.

Representative processes for the preparation of the compounds according to the present invention will now be described.

PREPARATION PROCESS 1

A compound represented by the general formula (I) wherein $R^2$ is an amino group can be prepared by the following process:

(Step 1)

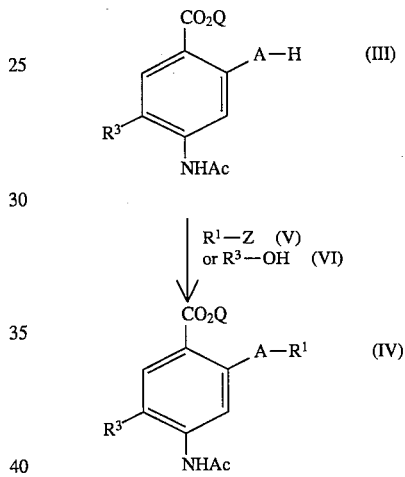

wherein $R^1$, $R^3$ and A are each as defined above; Q represents a lower alkyl, halogen-substituted lower alkyl, arylalkyl, arylalkenyl or aryl group; Z represents a halogen atom; and Ac represents an acetyl group.

In this step, a compound represented by the general formula (IV) is prepared by reacting a compound represented by the general formula (III) with a compound represented by the general formulas (V) or (VI).

Preferable example of the solvent include N,N-dimethylformamide and dimethyl sulfoxide when a compound (III) is reacted with a compound (V).

It is preferred that the reaction temperature ranges from 0° to 100° C. and the reaction time ranges from 30 minutes to 3 hours.

The reaction of a compound (III) with a compound (VI) is conducted by reacting triphenylphosphine with an azodicarboxylate either in a solvent such as tetrahydrofuran or benzene or in the absence of any solvent in an inert gas atmosphere preferably at a temperature of −80° to 0° C., adding a solution of the compound (VI) in tetrahydrofuran and a solution of the compound (III) in tetrahydrofuran to the obtained reaction mixture successively, and reacting the resulting mixture for 30 minutes to several hours while bringing the temperature to room temperature, thus giving a compound (IV).

(Step 2)

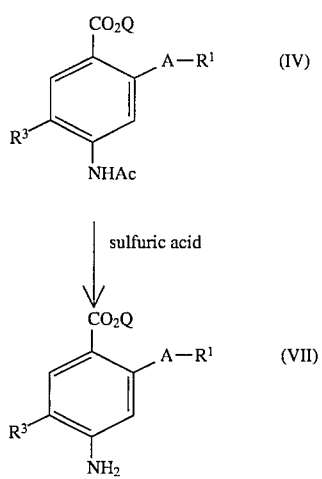

wherein $R^1$, $R^3$, A, Q and Ac are each as defined above.

In this step, the compound (IV) prepared in Step 1 is deacetylated. It is preferable that the sulfuric acid is used either in an equivalent amount or in excess.

The solvent to be used in the reaction is particularly preferably an alcoholic solvent such as methanol or ethanol.

The reaction temperature preferably ranges from about 0° to 50° C.

(Step 3)

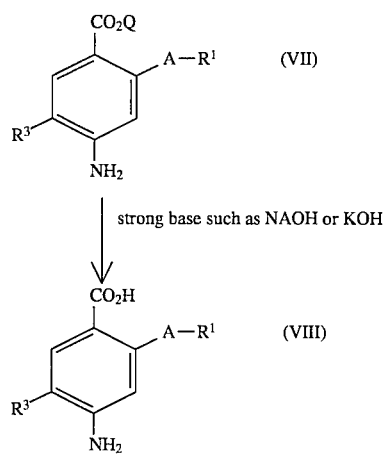

wherein $R^1$, $R^3$, A and Q are each as defined above.

In this step, the compound (VII) prepared in Step 2 is hydrolyzed.

The hydrolysis is conducted in the presence of two or more equivalents of a strong base such as sodium hydroxide or potassium hydroxide in an alcoholic solvent such as methanol or ethanol at room temperature to 100° C. for several hours, by which a compound (VIII) is obtained.

(Step 4)

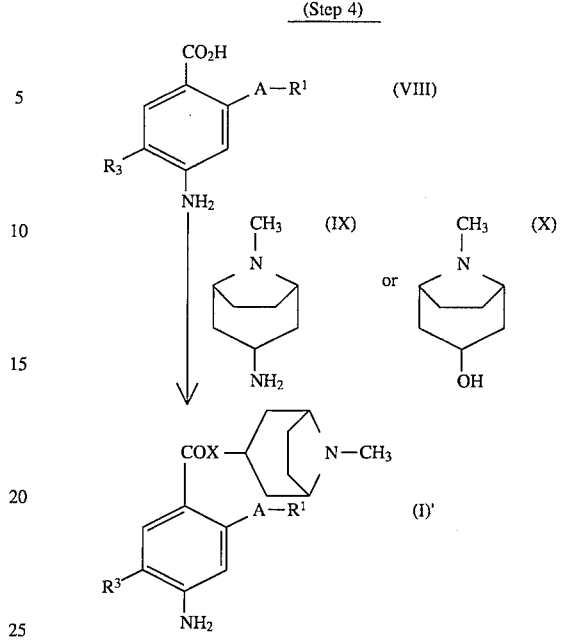

wherein $R^1$, $R^3$, A and X are each as defined above

In this step, a compound (I)' is prepared by condensing the compound (VIII) prepared in Step 3 with 3-aminotropane (IX) or tropine (X).

The condensation is conducted in the presence of a suitable dehydrating agent, for example, a carbodiimide such as dicyelohexylcarbodiimide. Alternatively, it may be conducted by converting the compound (VIII) into a reactive derivative thereof, such as an acid anhydride thereof, a conventional mixed acid anhydride (an acid anhydride comprising the compound (VIII) part and another carbonic acid part), an acid azide thereof, an active ester thereof with N-hydroxybenzotriazole-N-hydroxysuccinimide (a mixture of N-hydroxybenzotriazole with N-hydroxysuccinimide) or the like, or acid chloride thereof, and reacting the reactive derivative with the compounds (IX) or (X).

These reactions may be conducted either in the absence of any solvent or in the presence of a solvent inert to the reactions, e.g., benzene, toluene, xylene, tetrahydrofuran, chloroform, carbon tetrachloride, N,N-dimethylformamide or pyridine.

When the reactions are conducted in a solvent, the simultaneous use of an inorganic base such as sodium hydrogencarbonate, potassium carbonate, sodium carbonate or sodium hydroxide or an organic base such as triethylamine or pyridine gives more desirable results.

PREPARATION PROCESS 2

A compound represented by the general formula (I) wherein $R^2$ is an amino group can be prepared also by the following process:

(Step 1)

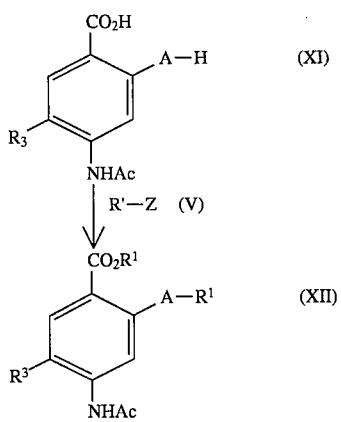

wherein $R^1$, $R^3$, A, Z and Ac are each as defined above.

In this step, a compound represented by the general formula (XII) is prepared by reacting a compound represented by the general formula (XI) with a compound represented by the general formula (V) in the presence of a base for several hours.

The base is preferably potassium carbonate or sodium carbonate, though any base is usable in this step.

Any solvent is usable with the proviso that the solvent is inert to the reaction.

The reaction temperature preferably ranges from about 0° to 100° C.

(Step 2)

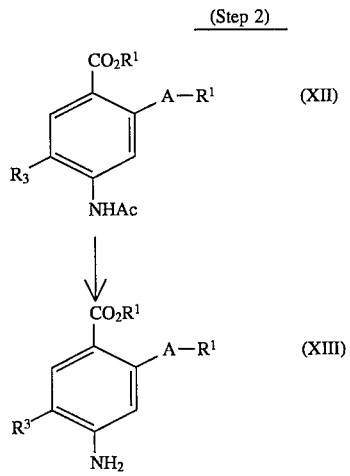

wherein $R^1$, $R^3$, A and Ac are each as defined above.

In this step, the compound (XII) prepared in Step 1 is deacetylated into a compound represented by the general formula (XIII).

The deacetylation may be conducted in a conventional manner, e.g., by treating the compound (XII) in a mixture comprising sulfuric acid in an equivalent amount or excess and a solvent such as methanol or ethanol for several hours.

The reaction temperature preferably ranges from about 0° to 50° C. in this case.

(Step 3)

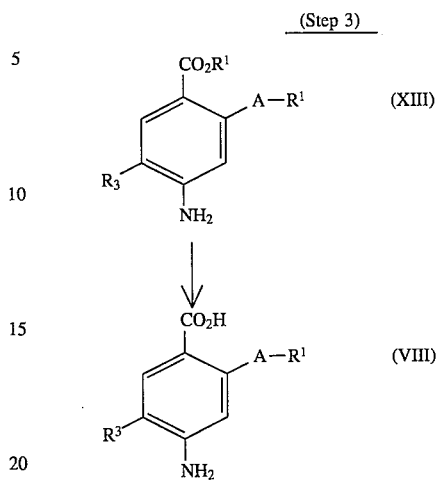

wherein $R^1$, $R^3$ and A are each as defined above.

In this step, the compound (XIII) prepared in Step 2 is hydrolyzed.

The hydrolysis may be conducted in a conventional manner, for example, by treating the compound (XIII) in an alcoholic solvent such as methanol or ethanol in the presence of two or more equivalents of a strong base such as sodium hydroxide or potassium hydroxide at a temperature ranging from room temperature to 100° C. for several hours.

(Step 4)

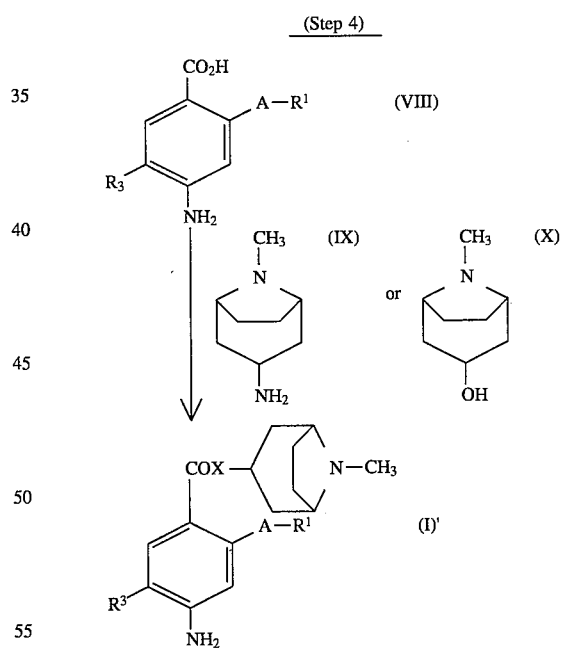

wherein $R^1$, $R^3$, A and X are each as defined above.

In this step, an objective compound (I)' is prepared in the same manner as that of Step 4 of Preparation process 1.

PREPARATION PROCESS 3

A compound represented by the general formula (I) wherein $R^2$ is a group selected from among those defined above with respect to $R^2$ except an amino group can be prepared by the following process:

(Step 1)

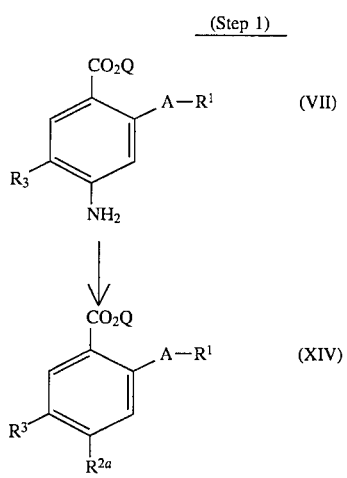

wherein $R^1$, $R^3$, A and Q are each as defined above; and $R^{2a}$ is a group selected from among those defined above with respect to $R^2$ except an amino group.

In this step, a compound represented by the general formula (VII) is acylated or alkylated into a compound represented by the general formula (XIV) in a conventional manner.

Examples of the process for acylating the compound (VII) include a process which comprises reacting the compound (VII) with a suitable acylating agent such as an acid chloride or acid anhydride; one which comprises conducting the acylation in the presence of a suitable dehydrating agent, e.g., a carbodiimide such as dicylohexylcarbodiimide; and one which comprises preparing a reactive derivative of a carboxylic acid giving a desired acyl group, that is, a reactive derivative of the compound (VII), for example, an acid azide thereof, a conventional mixed acid anhydride (an acid anhydride comprising the compound (VII) part and another carbonic acid part) or an active ester thereof with N-hydroxybenzotriazole-N-hydroxysuccinimide or the like, and treating the reactive derivative.

Examples of the process for alkylating the compound (VII) include one which comprises alkylating the compound (VII) with a suitable alkylating agent such as an alkyl halide or alkyl sulfonate; one which comprises reducing the acylamino derivative of the compound (VII) prepared by the above process with a reducing agent such as diborane; and one which comprises condensing the compound (VII) with a suitable aldehyde to form an imine (a compound having the group represented by the formula: —N=CH—R) and reducing the imine with a suitable reducing agent such as sodium borohydride.

The acylation or alkylation may be conducted either in the absence of any solvent or in the presence of a solvent inert to the reaction and examples of the solvent include benzene, toluene, xylene, tetrahydrofuran, chloroform, carbon tetrachloride, N,N-dimethylformamide and pyridine.

In some ease, more desirable results can be attained by conducting the acylation or alkylation in the presence of an inorganic base such as sodium hydrogencarbonate, potassium carbonate, sodium carbonate or sodium hydroxide or an organic base such as triethylamine or pyridine.

Further, when the alkylation of the compound (VII) is conducted through the condensation thereof with an aldehyde, more desirable results can be attained by conducting the reaction in the presence of ammonium acetate or the like.

(Step 2)

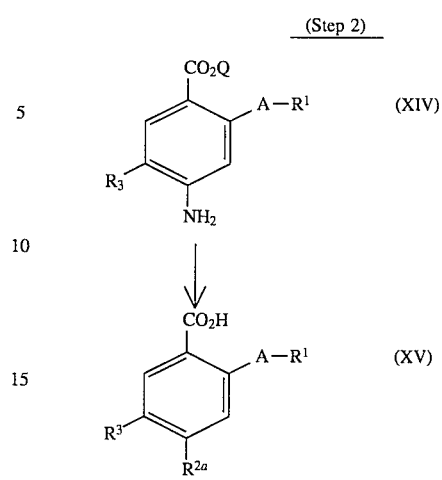

wherein $R^1$, $R^3$, A, Q and $R^{2a}$ are each as defined above.

In this step, the compound (XIV) prepared in Step 1 is hydrolyzed.

The hydrolysis is conducted in a conventional manner, for example, by treating the compound (XIV) in a suitable solvent such as methanol or ethanol in the presence of two or more equivalents of a base such as sodium hydroxide or potassium hydroxide for several hours to form a compound (XV).

The reaction temperature preferably ranges from room temperature to about 100° C.

(Step 3)

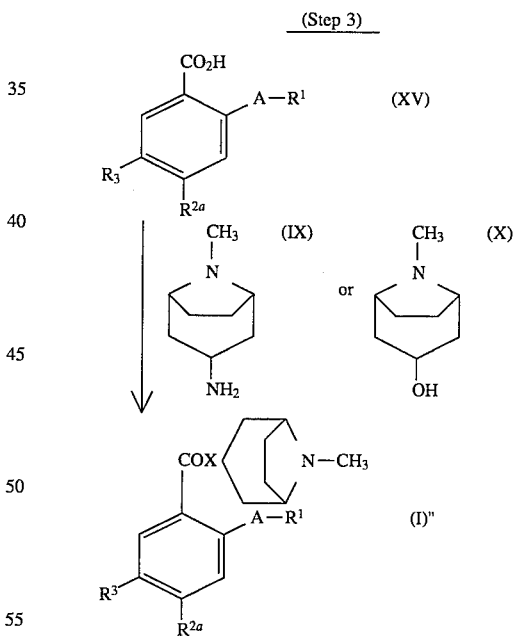

wherein $R^1$, $R^3$, A, X and $R^{2a}$ are each as defined above.

In this step, an objective compound (I)" is prepared by condensing the compound (XV) prepared in Step 2 with 3-aminotropane (IX) or tropine (X).

The condensation is conducted in the presence of a suitable dehydrating agent, for example, a carbodiimide such as dicyclohexylcarbodiimide. Alternatively, it may be conducted by converting the compound (XV) into a reactive derivative thereof such as an acid anhydride thereof, a conventional mixed acid anhydride (an acid anhydride comprising the compound (XV) part and another carbonic acid part), an acid azide thereof, an active ester thereof with N-hydroxybenzotriazole-N-hydroxysuccinimide or the like, or acid chloride thereof, and condensing the reactive derivative with the compounds (IX) or (X).

These reactions may be conducted either in the absence of any solvent or in the presence of a solvent inert to the reactions and examples of the solvent include benzene, toluene, xylene, tetrahydrofuran, chloroform, carbon tetrachloride, N,N-dimethylformamide and pyridine.

When the reactions are conducted in a solvent, the simultaneous use of an inorganic base such as sodium hydrogencarbonate, potassium carbonate, sodium carbonate or sodium hydroxide or an organic base such as triethylamine or pyridine gives more desirable results.

PREPARATION PROCESS 4

A compound represented by the general formula (I) wherein $R^2$ is a group selected from among those defined above with respect to $R^2$ except an amino group can be prepared also by the following process:

(Step 1)

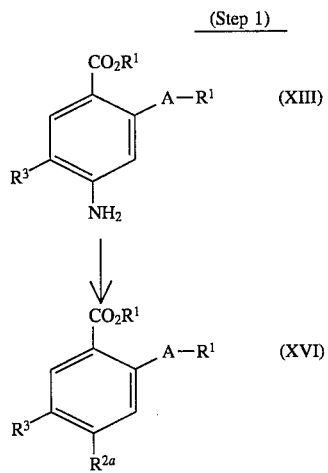

(Step 2)

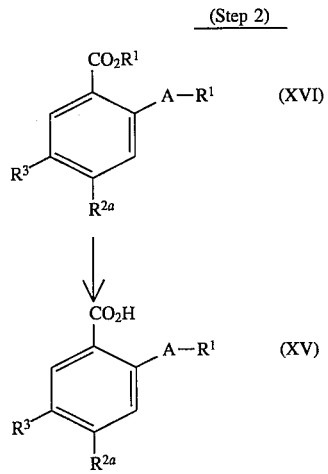

wherein $R^1$, $R^{2a}$, $R^3$ and A are each as defined above.

In this step, a compound (XIII) is acylated or alkylated into a compound (XVI) in a similar manner to that of Step 1 of Preparation process 3.

In this step, the compound (XVI) prepared in Step 1 is hydrolyzed into a compound (XV) in a similar manner to that of Step 2 of Preparation process 3.

(Step 3)

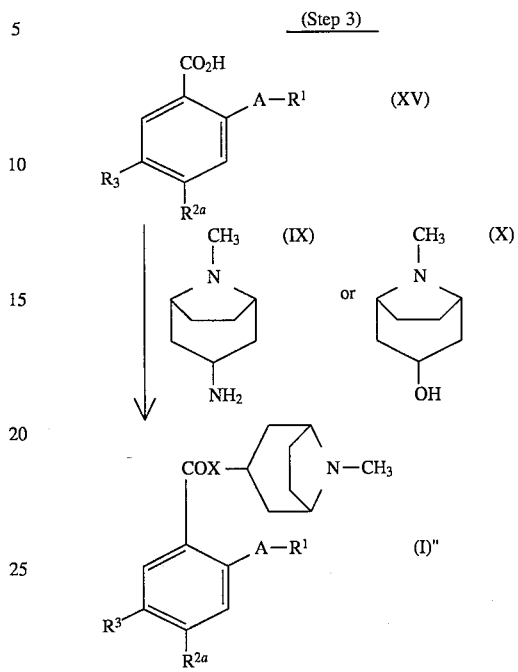

wherein $R^1$, $R^{2a}$, $R^3$, A and X are each as defined above.

In this step, an objective compound (I)" is prepared by condensing the compound (XV) prepared in Step 2 with 3-aminotropane (IX) or tropine (X) in a similar manner to that of Step 3 of Preparation process 3.

PREPARATION PROCESS 5

A compound represented by the general formula (I) wherein $R^2$ is a group selected from among those defined above with respect to $R^2$ except an amino group can be prepared also by the following process:

(Step 1)

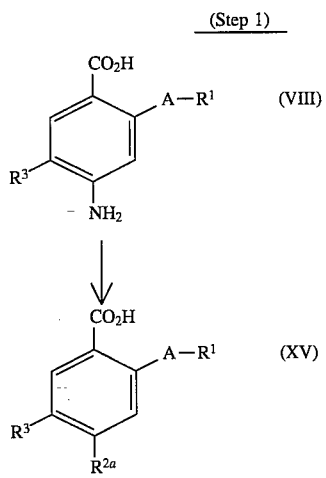

wherein $R^1$, $R^{2a}$, $R^3$ and A are each as defined above.

In this step, a compound (VIII) is acylated or alkylated into a compound (XV) in a conventional manner.

Examples of the conventional process for acylating the compound (VIII) include one which comprises reacting the compound (VIII) with a suitable acylating agent such as an acid chloride or an acid anhydride; one which comprises conducting the acylation in the presence of a suitable dehydrating agent, e.g., a carbodiimide such as dicylohexylcarbodiimide; and one which comprises preparing a reactive derivative of a carboxylic acid giving a desired acyl group, that is, a reactive derivative of the compound (VIII), for example, an acid azide thereof, a conventional mixed acid anhydride (an acid anhydride comprising the compound (VIII) part and another carbonic acid part) or an active ester thereof with N-hydroxybenzotriazole-N-hydroxysuccinimide or the like, and treating the reactive derivative.

Examples of the conventional process for alkylating the compound (VIII) include one which comprises alkylating the compound (VIII) with a suitable alkylating agent such as an alkyl halide or alkyl sulfonate; one which comprises condensing the compound (VIII) with a suitable aldehyde to form an imine and reducing the imine with a suitable reducing agent such as sodium borohydride; and one which comprises reducing the acyl derivative of the compound (VIII) prepared by the above-described acylating process with a reducing agent such as diborane.

The above alkylation and acylation may be conducted either in the absence of any solvent or in the presence of a solvent inert to each reaction and examples of the solvent include benzene, toluene, xylene, tetrahydrofuran, chloroform, carbon tetrachloride. N,N-dimethylformamide and pyridine.

Further, more desired results can be attained by conducting these reactions in the presence of an inorganic base such as sodium hydrogencarbonate, potassium carbonate, sodium carbonate or sodium hydroxide or an organic base such as triethylamine or pyridine.

Furthermore, when the alkylation of the compound (VIII) is conducted through the reduction of the imine prepared by the condensation of the compound (VIII) with a suitable aldehyde, more desirable results can be attained by conducting the condensation in the presence of ammonium acetate.

(Step 2)

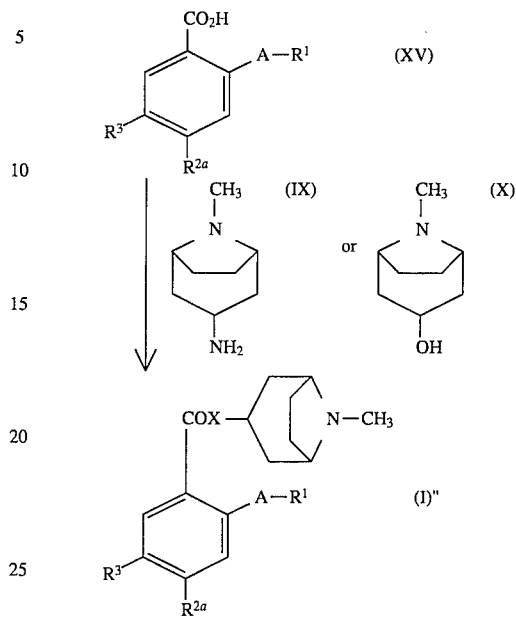

wherein $R^1$, $R^{2a}$, $R^3$, A and X are each as defined above.

In this step, an objective compound (I)" is prepared by condensing the compound (XV) prepared in Step 1 with 3-aminotropane (IX) or tropine (X) in a similar manner to that of Step 3 of Preparation processes 3 or 4.

All of the Preparation processes described above are illustrated by the following reaction scheme, wherein "Prepn. process 1—1", for example, refers to the reaction described in Step 1 of Preparation process 1.

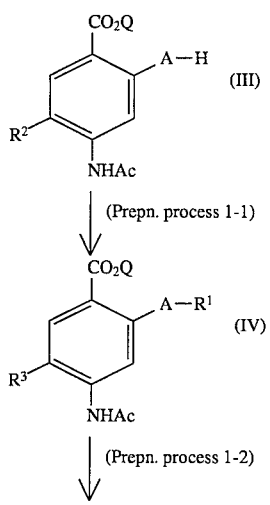

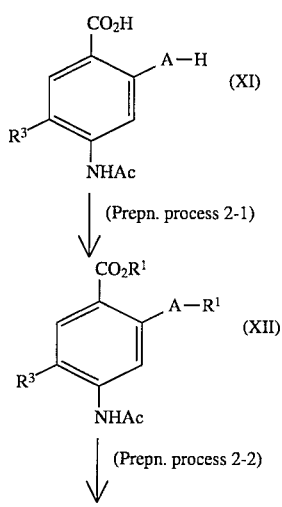

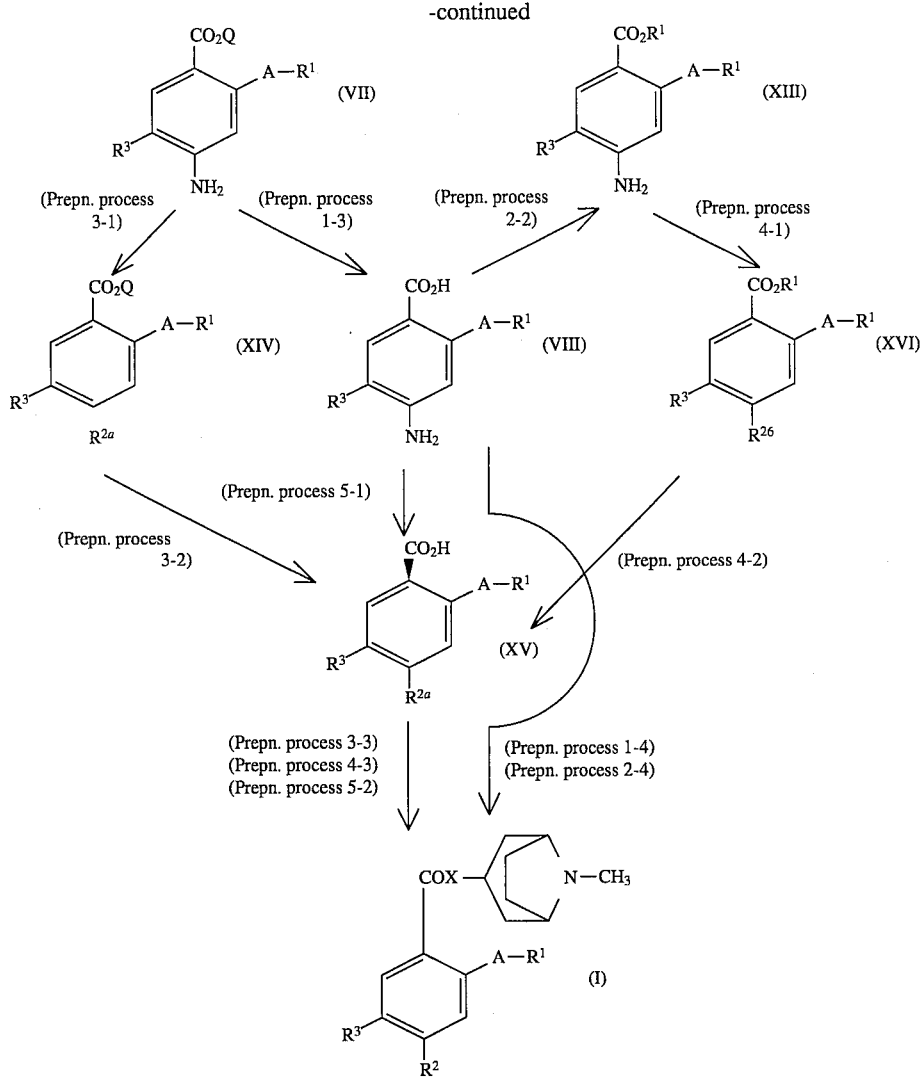

EXPERIMENTAL EXAMPLES

Experimental Examples will now be described to illustrate the effects of the compounds according to the present invention in detail.

EXPERIMENTAL EXAMPLE 1

Antagonism against 2-methylserotonin-induced contraction or systole of ileum

This experiment was made according to the method of Sanger et al. [see Eur. J. Pharmacol., 159, 113–124 (1989)]. The nonterminal ileum of a Hartley male guinea pig was suspended in the Krebs-Henseleit solution (37° C.) by applying a load of 0.5 g to the end of the ileum and a gaseous mixture comprising 95% of oxygen and 5% of carbon dioxide was passed through the solution. The contraction of the ileum was isometrically determined. After allowing the ileum to stand for one or more hours for stabilization, a solution of a test compound was added to the solution, and after 30 minutes, 2-methylserotonin was noncumulatively added. The pA2 value was calculated from the rightward shift of the dose-response curve of the 2-methylserotonin-induced contraction caused by the test compound according to the method of Rossum et al. [see Arch. Int. Pharmacodyn., 143, 299(1963)]. BRL 24682 was used as a control in this experiment.

The results are given in Table 1.

TABLE 1

| Test compd. (Ex. compd.) | pA2 |
|---|---|
| 2 | 8.68 |
| 4 (−)-isomer | 8.57 |
| 36 (+)-isomer | 8.72 |
| 38 (+)-isomer | 9.02 |
| 21 | 8.46 |
| 25 | 9.05 |
| 26 | 9.33 |
| 27 | 9.39 |
| 29 | 9.34 |
| 32 | 9.03 |
| 33 | 8.21 |
| 42 (+)-isomer | 8.92 |
| BRL 24682 | 7.80 |

EXPERIMENTAL EXAMPLE 2

Activity against cisplatin-induced vomiting of beagle

Beagles weighing 7 to 12 kg were used. 3 mg/kg of cisplatin (a product of Sigma) (1 ml/kg of physiological saline) was administered to each beagle through the vein of its forefoot. One hour after the administration of cisplatin, physiological saline (0.2 ml/kg) was administered to a control group of beagles and a solution of a test compound in physiological saline was administered to a test group of beagles, each through the vein of the other forefoot. The frequency of vomiting observed over a 5-hour period from the administration of cisplatin was recorded and the inhibitory ratio of the test compound was calculated according to the following formula.

The results are given in Table 2.

TABLE 2

$$\text{Inhibitory ratio (\%)} = \left[1 - \frac{\text{average frequency of test group}}{\text{average frequency of control group}}\right] \times 100$$

| Test compd.<br>(Ex. compd.) | Inhibitory ratio against cisplatin-induced vomiting (%) | | |
|---|---|---|---|
| | 0.03 mg/kg | 0.1 mg/kg | 0.3 mg/kg |
| 4 (−)-isomer | 37 | 78 | |
| 21 | | | 100 |
| 42 (+)-isomer | 59 | 92 | |

EXPERIMENTAL EXAMPLE 3

Activity for raising gastric emptying function

This experiment was made according to the method of Decktor et al. [see Eur. J. Pharmacol., 147, 313–316 1988)]. Fischer male rats (weight: 160 to 180 g) were fasted for 18 hours before 3 ml of a test food comprising methylcellulose, beef broth, casein, sugar and corn starch was orally administered to each rat. One hour after the administration, the stomach was extirpated from each rat. The gastric emptying ratio was calculated from the weight of the test food remaining in the stomach. The ratio of rise of the gastric emptying function was determined by comparing the gastiric emptying ratio of a medicated rat with that of a control rat which had not administered any test compounds. Each test compound (5 ml/kg) was orally administered one hour before the administration of the test food. BRL 24682 was used as a control in this experiment.

The results are given in Table 3.

TABLE 3

| Test compd.<br>(Ex. compd.) | Ratio of rise of gastric emptying function (%) |
|---|---|
| 2 | 24.5 |
| 4 (−)-isomer | 31.1 |
| 37 (−)-isomer | 15.3 |
| 38 (+)-isomer | 20.5 |
| 21 | 18.9 |
| 24 | 13.2 |
| 25 | 26.3 |
| 27 | 17.2 |
| 29 | 20.6 |
| 32 | 18.3 |
| 40 racemic modification | 16.2 |
| 42 (+)-isomer | 22.2 |
| 43 (−)-isomer | 12.9 |
| BRL 24682 | 12.9 |

EXPERIMENTAL EXAMPLE 4

Effect of increasing contraction of guinea pig ileum induced by electrical field stimulation This experiment was made according to the method of Sanger et al. [see Br. J. Pharmacol., 91, 77–87 (1987)]. The longitudinal muscle of the nonterminal ileum of a guinea pig was separated and vertically suspended in the Krebs-Henseleit solution (37° C.) in a Magnus tube by applying a load of 0.5 g to the end of the muscle. A mixed gas comprising 95% of oxygen and 5% of carbon dioxide was passed through the solution. The contraction of the muscle was isometrically determined. Electrical field stimulation was applied to the muscle by the use of a platinum electrode once per 10 seconds to induce the contraction of the muscle. The contraction was caused through the release of acetylcholine. After the muscle had been stabilized, a solution of a test compound was cumulatively added into the Magnus tube at intervals of 10 minutes. The effect of the test compound is represented by percentage based on the initial contraction. The minimum concentration of each test compound at which an increment was found in the contraction due to the release of acetylcholine is shown in Table 4.

TABLE 4

| Test compd.<br>(Ex. compd.) | Min. concn. causing increment of ileal contraction (μM) |
|---|---|
| 21 | 0.052 |
| 46 | 0.16 |
| 22 | >100 |
| 23 | >100 |
| 24 | 0.17 |
| 20 racemic modification | 0.11 |
| 37 (+)-isomer | 0.048 |
| 38 (−)-isomer | 0.13 |
| 2 racemic modification | 0.05 |
| 4 (+)-isomer | 0.056 |
| 36 (−)-isomer | 0.26 |
| 40 racemic modification | 0.22 |
| 42 (+)-isomer | 0.086 |
| 43 (−)-isomer | 0.47 |
| 25 | 1.0 |
| 26 | >100 |
| 27 | 0.25 |
| 28 | >100 |
| 29 | 0.26 |
| 30 | 0.038 |
| 31 | >100 |
| 32 | >100 |
| 33 | 1.8 |
| BRL 24682 | 0.086 |

It can be understood from the results of the above pharmacological experiments that the compound of the present invention has a 5-HT$_3$ antagonism and an ACh release accelerating activity and is therefore effective in raising the gastrointestinal functions such as gastric emptying function and useful as an antiemetic.

Accordingly, the compound of the present invention acts as a 5-HT$_3$ antagonism and an ACh release accelerator to be useful as a drug based on these activities.

The acetylcholine release accelerating activity is based on a 5-HT$_4$ agonist of the compound according to the present invention.

The compound of the present invention is efficacious for various diseases and specific examples of the diseases include irritable bowel syndrome; reflux esophagitis; gastrointestinal symptoms (such as heartburn, anorexia, nausea, vomiting, abdominal pain and abdominal distension) caused by chromic gastritis, gastroptosis, postgastrectomy syndrome or the like; gastrointestinal symptoms and gastrointestinal insufficiency represented by those caused by the administration of an anticancer drug or irradiation with radiation; anxiety; migraine; amnestic syndrome; senile dementia; Alzheimer disease; and dependence. Particularly, the compound of the present invention is excellent in the balance between 5-HT$_3$ antagonism and ACh release accelerating activity, so that it is extremely efficacious for gastrointestinal symptoms and gastrointestinal insufficiency.

Further, the compound of the present invention is less toxic and highly safe, thus being valuable also in this sense.

When the compounds prepared in the following Examples 4 and 43 were each orally administered to a rat for one week, no toxicity was exhibited in a dose of up to 30 mg/kg.

Further when the above two compounds were each orally administered to a beagle, no toxicity was exhibited in a dose of up to 1.5 mg/kg.

The compound of the present invention is administered as a therapeutic and preventive agent for the above diseases in the form of tablet, powder, granule, capsule, syrup or inhalant. Although the dose thereof remarkably varies depending upon the extent of symptom, age and the kind of disease, the dose per adult a day is about 0.01 to 1000 mg, preferably 0.1 to 500 mg, still preferably 0.1 to 100 mg, which may be administered in one to several portions a day.

When the compound of the present invention is administered as an injection, the dose is generally 1 to 3000 μg/kg, preferably about 3 to 1000 μg/kg.

The preparations according to the present invention are prepared by the use of conventional carriers in conventional manners.

More precisely, a solid preparation for oral administration according to the present invention is prepared by adding a filler and, if necessary, a binder, disintegrator, lubricant, coloring matter and/or corrigent to an active ingredient and shaping the obtained mixture into a tablet, coated tablet, granule, powder or capsule in conventional manners.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the coloring matter include those authorized as pharmaceutical additives; and those of the corrigent include cocoa powder, mentha herb, aromatic powder, mentha oil, borneol and powdered cinnamon bark. Of course, the tablet and granule may be suitably coated with sugar, gelatin or the like, if necessary.

An injection according to the present invention is prepared by adding a pH regulator, buffer, stabilizer and/or solubilizing agent to an active ingredient at need and formulating the mixture into an injection for subcutaneous, intramuscular or intravenous administration by a conventional process.

EXAMPLES

Examples according to the present invention will now be described, though the present invention is not limited to them.

In the Examples, Me represents a methyl group and Ac an acetyl group.

EXAMPLE A

Metyl 4-acetoamido-5-chloro-2-{(3-pentyn-2-yl)oxy}benzoate

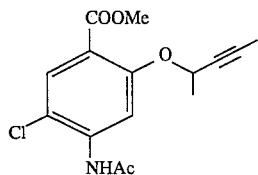

Triphenylphosphine (146.4 g) was dissolved in tetrahydrofuran (500 ml). To the obtained solution, at −65° C. under nitrogen stream, diethylazocarboxylate (97.2 g), 3-pentyn-2-ol (33.2 g) and a solution of methyl 4-acetoamido-5-chlorosalicylate (80 g) in tetrahydrofuran (1.4 l) were gradually dropped in this order. The temperature of the reaction mixture was raised to room temperature, and the reaction mixture was stirred over night at room temperature. The solvent was removed under reduced pressure. Residue was dissolved in ethyl acetate (200 ml) and n-hexane (1.3 l) was dropwisely added under stirring. Crystal thus precipitated was filtered off, and the filtrate was concentrated in vacuo. The residue was purified by silica gel column chromatography to give 74.3 g of the title compound.

$^1$H-NMR (400 MHz, CDCl$_3$) δ ppm; 1.65 (d, J=5.5 Hz, 3H), 1.82 (d, J=2.0 Hz, 3H), 2.26 (s, 3H), 3.86 (s, 3H), 4.85–4.94 (m, 1H), 7.72 (bs, 1H), 7.88 (s, 1H), 8.46 (s, 1H)

EXAMPLE B

Methyl 4-amino-5-chloro-2-{(3-pentyn-2-yl)oxy}benzoate

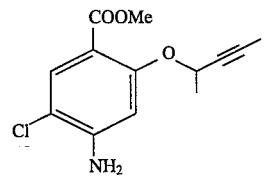

To the suspension of methyl 4-acetoamido-5-chloro-2-{(3-pentyn-2-yl)oxy}benzoate (73.3 g) in methanol (700 ml), concentrated sulfuric acid (73 ml) was dropwisely added at 0° C. The temperature of the reaction mixture was raised to room temperature. After the reaction mixture was stirred over night at room temperature, the reaction mixture was poured into a saturated aqueous sodium hydrogencarbonate solution (5 l) gradually. Crystal thus precipitated was recovered by filtration, washed with water and dried to obtain 66.5 g of the title compound as colorless crystal.

$^1$H-NMR (400 MHz, CDCl$_3$) δ ppm; 1.66 (d, J=6.5 Hz, 3H), 1.81 (d, J=2.0 Hz, 3H), 3.81 (s, 3H), 4.41 (bs, 2H), 4.70–4.78 (m, 1H), 6.53 (s, 1H), 7.82 (s, 1H)

EXAMPLE C

4-Amino-5-chloro-2-{(3-pentyn-2-yl)oxy}benzoic acid

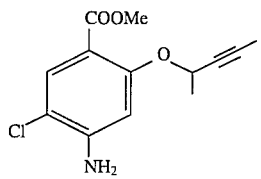

To the suspension of methyl 4-amino-5-chloro-2-{(3-pentyn-2-yl)oxy}benzoate (56.0 g) in methanol (1.3 l), aqueous sodium hydroxide (5N) solution (140 ml) was added. The resultant mixture was stirred for 6 hours at 50° C., and then 3 days at room temperature. To the obtained mixture, water (1 l) was added, followed by acidification with 2N hydrochloric acid. Crystal thus precipitated was recovered by filtration, washed with water and dried to obtain 51.5 g of the title compound as colorless crystal.

$^1$H-NMR (400 MHz, CDCl$_3$) δ ppm: 1.50 (d, J=6.5 Hz, 3H), 1.79 (d, J=2.0 Hz, 3H), 4.81–4.84 (m, 1H), 6.07 (bs, 2H), 6.53 (s, 1H), 7.56 (s, 1H) m.p.; 114°–116° C.

EXAMPLE D (S)-4-Amino-5-chloro-2-{(3-pentyn-2-yl)oxy} benzoic acid

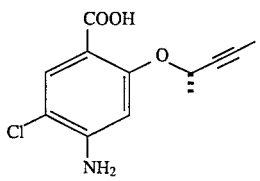

(±)-4-Amino-5-chloro-2-{(3-pentyn-2-yl)oxy}benzoic acid (15.2 g) was dissolved in ethanol (105 ml), and (+)-dehydroabiethylamine (17.1 g) solution in ethanol (15 ml) was added to the obtained solution at room temperature. The resultant mixture was set on the table for 2 hours. Crystal thus precipitated was recovered by filtration, and washed with a small amount of ethanol. Then, the crystal was dissolved in aqueous sodium hydroxide (1N) solution, and extraction with dichloromethane was conducted. The aqueous phase was acidified with concentrated hydrochloric acid, then extracted with chloroform. The organic phase was dried and concentrated in vacuo to give 4.23 g of white crystal.

This crystal was dissolved in ethyl acetate (70 ml), and (S)-(−)-naphthylethylamine (2.67 ml) was added to the resultant solution. The mixture thus obtained was set on the table for 1 hour. Crystal thus precipitated was recovered by filtration, and washed with a small amount of ethyl acetate. Then, the crystal was dissolved in 1N hydrochloric acid, and extraction with chloroform was conducted. The organic phase was dried and concentrated in vacuo to give 2.23 g of white crystal.

Furthermore, this crystal was dissolved in ethyl acetate (45 ml) again, and (S)-(−)-naphthylethylamine (1.41 ml) was added to the resultant solution. The mixture thus obtained was set on the table for 1 hour. Crystal thus precipitated was recovered by filtration, and washed with a small amount of ethyl acetate. Then, the crystal was dissolved in 1N hydrochloric acid, and extraction with chloroform was conducted. The organic phase was dried and concentrated in vacuo to give 1.50 g (99.6% ee) of the title compound as white crystal.

EXAMPLE 1 endo-4-Amino-5-chloro-N-(8-methyl-8-azabicyclo[3.2.1]oct-3-yl)-2-{(3-pentyn-2-yl)oxy}benzamide

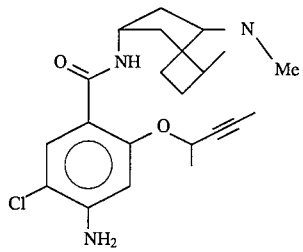

400 mg of 4-amino-5-chloro-2-{(3-pentyn-2-yl)oxy}benzoic acid and 400 mg of endo-3-amino-8-methyl-8-azabicyclo[3.2.1]octane were dissolved in 20 ml of pyridine, followed by the addition of 0.38 ml of a 5N aqueous solution of sodium hydroxide under stirring at room temperature. the obtained mixture was stirred for 10 minutes, followed by the addition of 650 mg of 1,3-dicyclohexylcarbodiimide. The obtained mixture was stirred at room temperature for 8 hours, followed by the addition of 30 ml of water. The resulting mixture was filtered to remove insolubles and the filtrate was basified with an aqueous solution of sodium hydroxide and extracted with chloroform. The organic phase was dried over anhydrous magnesium sulfate and distilled to remove the solvent. The residue was purified by silica gel chromatography (10% methanol/chloroform) to give 450 mg of the title compound as a white crystal.

$^1$H-NMR (400 MHz, d$_6$-DMSO) δ ppm; 1.56–1.65 (m, 5H), 1.75–1.85 (m, 5H), 1.95–2.13 (m, 4H), 2.18 (s, 3H), 3.00–3.13 (m, 2H), 3.93–4.00 (m, 1H), 5.05–5.13 (m, 1H), 5.89 (bs, 2H), 6.59 (s, 1H), 7.70 (s, 1H), 7.87 (d, J=6.0 Hz, 1H) m.p.; 173°–175° C.

EXAMPLE 2 endo-4-Amino-5-chloro-N-(8-methyl-8-azabicyclo[3.2.1]oct-3-yl)-2-{(3-pentyn-2-yl)oxy}benzamide hydrochloride

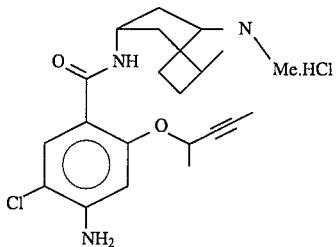

450 mg of endo-4-amino-5-chloro-N-(8-methyl-8-azabicyclo[3.2.1]oct-3-yl)-2-{(3-pentyn-2-yl)oxy}benzamide was dissolved in 5 ml of ethanol, followed by the addition of ethanolic hydrochloric acid and diethyl ether in this order. A salt thus precipitated was recovered by filtration. 320 mg of the title compound was obtained as a palely orange crystal.

$^1$H-NMR (400 MHz, d$_6$-DMSO) δ ppm; 1.60 (d, J=6.5 Hz, 3H), 1.82 (d, J=2.0 Hz, 3H), 1.98–2.48 (m, 8H), 2.64 (d, J=6.0 Hz, 3H), 3.75–3.93 (m, 2H), 3.95–4.05 (m, 1H), 5.05–5.13 (m, 1H), 5.95 (bs, 2H), 6.61 (s, 1H), 7.63 (s, 1H), 7.92 (d, J=5.0 Hz, 1H)

EXAMPLE 3

(−)-endo-4-Amino-5-chloro-N-(8-methyl-8-azabicyclo[3.2.1]oct-3-yl)-2-{(3-pentyn-2-yl)oxy}benzamide (+)-endo-4-Amino-5-chloro-N-(8-methyl-8-azabicyclo[3.2.1]oct-3-yl)-2-{(3-pentyn-2-yl)oxy}benzamide

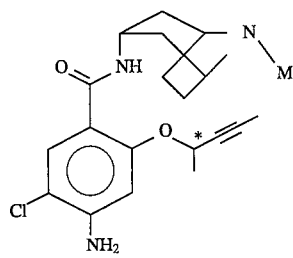

800 mg of the racemic modification prepared in the Example 2 was subjected to high performance liquid chromatography (HPLC) using a chiral column (a product of Daicel Chemical Industries, Ltd.; CHIRALCEL OD) and a mobile phase solvent (ethanol:hexane:triethylamine= 20:80:0.1) to give 370 mg of the (−)-isomer and 800 mg of the (+)-isomer.

(−)-isomer $^1$H-NMR (400 MHz, CDCl$_3$) δ ppm; 1.68–1.83 (m, 5H) 1.84 (d, J=3.0 Hz, 3H), 1.85–1.95 (m, 2H), 2.05–2.15 (m, 2H), 2.20–2.29 (m, 2H), 2.30 (s, 3H), 3.11–3.18 (m, 2H), 4.18–4.25 (m, 1H), 4.35 (bs, 2H), 4.93 (qq, J=3.0, 7.0 Hz, 1H), 6.46 (s, 1H), 7.98 (d, J=5.5 Hz, 1H), 8.09 (s, 1H)

(+)-isomer $^1$H-NMR (400 MHz, CDCl$_3$) δ ppm; 1.66–1.79 (m, 5H) 1.84 (d, J=3.0 Hz, 3H), 1.85–1.94 (m, 2H), 2.06–2.15 (m, 2H), 2.20–2.31 (m, 2H), 2.32 (s, 3H), 3.10–3.18 (m, 2H), 4.16–4.24 (m, 1H), 4.93 (qq, J=3.0, 7.0 Hz, 1H), 6.46 (s, 1H), 7.98 (d, J=5.5 Hz, 1H), 8.08 (s, 1H) m.p.; 144°–145° C.

EXAMPLE 4

(−)-endo-4-Amino-5-chloro-N-(8-methyl-8-azabicyclo[3.2.1]oct-3-yl)-2-{(3-pentyn-2-yl)oxy}benzamide hydrochloride

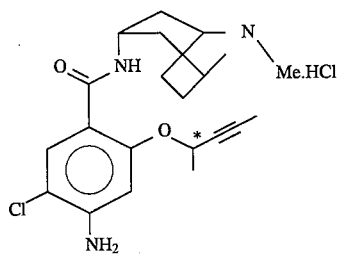

1.85 g of (−)-endo-4-amino-5-chloro-N-(8-methyl-8-azabicyclo[3.2.1]oct-3-yl)-2-{(3-pentyn-2-yl)oxy}benzamide was dissolved in 9 ml of ethanol, followed by the addition of 2.46 ml of 2N hydrochloric acid and ml of water in this order. The obtained mixture was freeze-dried to give 1.99 g of the title (−)-isomer hydrochloride.

MZ m/z (FAB); 376 (M$^+$+1) $^1$H-NMR (400 MHz, d$_6$-DMSO) δ ppm; 1.62 (d, J=6.5 Hz, 3H), 1.84 (d, J=2.0 Hz, 3H), 2.03–2.45 (m, 8H), 2.67 (d, J=5.0 Hz, 3H), 3.82–3.91 (m, 2H), 4.00–4.05 (m, 1H), 5.10–5.14 (m, 1H), 5.96 (bs, 2H), 6.63 (s, 1H), 7.66 (s, 1H), 7.93 (d, J=5.0 Hz, 1H), 9.92 (s, 1H)

EXAMPLES 5 TO 19

The following compounds were prepared in a similar manner to that of the Example 1.

EXAMPLE 5 endo-4-Amino-5-chloro-N-(8-methyl-8-azabicyclo[3.2.1]oct-3-yl)-2-{(1-pentyn-3-yl)oxy}benzamide

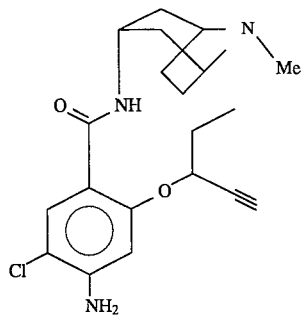

$^1$H-NMR (400 MHz, d$_6$-DMSO) δ ppm; 1.03 (t, J=8.0 Hz, 3H), 1.52 (t, J=12.0 Hz, 2H), 1.68–1.74 (m, 2H), 1.84–2.12 (m, 6H), 2.14 (s, 3H), 3.03 (bs, 2H), 3.93–4.02 (m, 1H), 4.94 (t, J=4.0 Hz, 1H), 5.94 (s, 2H), 6.60 (s, 1H), 7.67 (s, 1H), 7.78 (d, J=6.0 Hz, 1H) m.p.; 182°–184° C.

EXAMPLE 6 endo-4-Amino-5-chloro-N-(8-methyl-8-azabicyclo[3.2.1]oct-3-yl)-2-propargyloxybenzamide

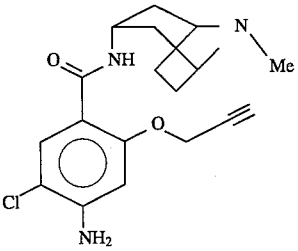

$^1$H-NMR (400 MHz, d$_6$-DMSO) δ ppm; 1.50–1.70 (m, 2H), 1.75–1.90 (m, 2H), 1.93–2.13 (m, 4H), 2.22 (s, 3H), 3.10–3.20 (m, 2H), 3.71 (t, J=2.0 Hz, 1H), 3.94–4.01 (m, 1H), 4.88 (d, J=2.0 Hz, 2H), 5.99 (bs, 2H), 6.52 (s, 1H), 7.67 (s, 1H), 7.99 (d, J=5.0 Hz, 1H)

EXAMPLE 7 endo-4-Amino-2-(2-butynyloxy)-5-chloro-
N-(8-methyl-8-azabicyclo[3.2.1]oct-3-yl)benzamide

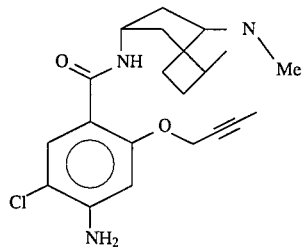

$^1$H-NMR (400 MHz, d$_6$-DMSO) δ ppm; 1.51–1.58 (m, 2H), 1.75–1.83 (m, 2H), 1.84 (t, J=2.5 Hz, 3H), 1.95–2.10 (m, 4H), 2.15 (s, 3H), 3.00–3.03 (m, 2H), 3.96–3.98 (m, 1H), 4.82 (q, J=2.5 Hz, 2H), 5.97 (s, 2H), 6.50 (s, 1H), 7.69 (s, 1H), 8.06 (d, J=7.0 Hz, 1H) m.p.; 188°–191° C.

EXAMPLE 8 endo-4-Amino-5-chloro-N-(8-methyl-
8-azabicyclo[3.2.1]oct-3-yl)-
2-(3-pentynyloxy)benzamide

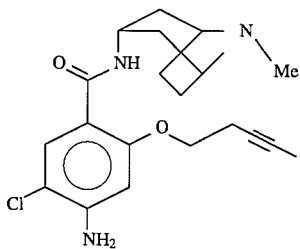

$^1$H-NMR (400 MHz, d$_6$-DMSO) δ ppm; 1.58–1.88 (m, 2H), 1.71 (t, J=2.5 Hz, 3H), 1.73–1.80 (m, 2H), 1.90–2.10 (m, 4H), 2.66 (tq, J=6.5, 2.5 Hz, 2H), 3.00–3.10 (m, 2H), 3.95–3.97 (m, 1H), 4.12 (t, J=6.5 Hz, 2H), 5.90 (s, 2H), 6.49 (s, 1H), 7.70 (s, 1H), 7.90 (d, J=6.5 Hz, 1H)

EXAMPLE 9 endo-4-Amino-2-{(3-butyn-2-yl)oxy}-
5-chloro-N-(8-methyl-8-azabicyclo[3.2.1]oct-
3-yl)benzamide

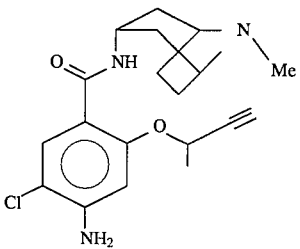

$^1$H-NMR (400 MHz, d$_6$-DMSO) δ ppm; 1.52–1.60 (m, 2H), 1.64 (d, J=6.5 Hz, 3H), 1.71–1.78 (m, 2H), 1.95–2.08 (m, 4H), 2.13 (s, 3H), 2.97–3.03 (m, 2H), 3.70 (d, J=3.0 Hz, 1H), 3.93–3.99 (m, 1H), 5.14 (dq, J=3.0, 6.5 Hz, 1H), 5.97 (bs, 2H), 6.59 (s, 1H), 7.68 (s, 1H), 7.81 (d, J=6.5 Hz, 1H)

EXAMPLE 10 endo-4-Amino-5-chloro-2-{(4-heptyn-3-yl)
oxy}-N-(8-methyl-
8-azabicyclo[3.2.1]oct-3-yl)benzamide

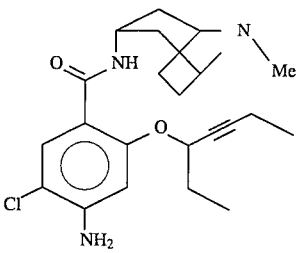

$^1$H-NMR (400 MHz, CDCl$_3$) δ ppm; 1.10 (t, J=8.0 Hz, 3H), 1.12 (t, J=8.0 Hz, 3H), 1.71–2.31 (m, 12H), 2.32 (s, 3H), 3.16 (bs, 2H), 4.20 (dd, J=4.0, 11.0 Hz, 1H), 4.35 (bs, 2H), 4.73–4.78 (m, 1H), 6.43 (s, 1H), 7.98 (bs, 1H), 8.09 (s, 1H)

EXAMPLE 11 endo-4-Amino-5-chloro-2-{(4-heptyn-2-yl)oxy}-
N-(8-methyl-8-azabicyclo[3.2.1]oct-3-yl)benzamide

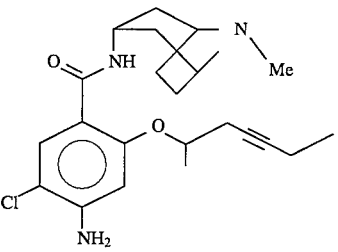

$^1$H-NMR (400 MHz, CDCl$_3$) δ ppm; 1.10 (t, J=7.5 Hz, 3H), 1.52 (d, J=6.0 Hz, 3H), 1.74–1.92 (m, 6H), 2.08–2.18 (m, 3H), 2.26–2.34 (m, 1H), 2.33 (s, 3H), 2.52 (A$_2$BX type, J=2.5, 7.5, 16.0 Hz, 1H), 2.64 (A$_2$BX type, J=2.5, 2.5, 16.0 Hz, 1H), 3.20 (bs, 2H), 4.16–4.24 (m, 1H), 4.33 (br s, 2H), 4.52–4.63 (m, 1H), 6.32 (s, 1H), 7.96 (bs, 1H), 8.10 (s, 1H)

EXAMPLE 12 endo-4-Amino-5-chloro-2-{(2-hexyn-4-yl)oxy}-
N-(8-methyl-8-azabicyclo[3.2.1]oct-3-yl)benzamide

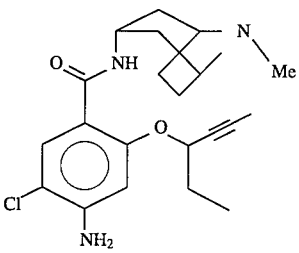

$^1$H-MHz, d$_6$-DMSO) δ ppm; 1.02 (t, J=7.5 Hz, 3H), 1.50–1.63 (m, 2H), 1.70–1.80 (m, 2H), 1.83 (d, J=2.0 Hz, 3H), 1.85–2.13 (m, 6H), 2.16 (s, 3H), 3.00–3.10 (m, 2H), 3.91–4.00 (m, 1H), 4.88–4.94 (m, 1H), 5.92 (bs, 2H), 6.58 (s, 1H), 7.68 (s, 1H), 7.85 (d, J=6.0 Hz, 1H)

EXAMPLE 13 endo-4-Amino-5-chloro-2-{(3-hexyn-2-yl)oxy}-
N-(8-methyl-8-azabicyclo[3.2.1]oct-3-yl)benzamide

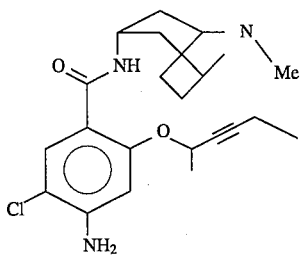

¹H-NMR (400 MHz, d₆-DMSO+CDCl₃) δ ppm; 1.02 (t, J=7.5 Hz, 3H), 1.55–1.65 (m, 5H), 1.73–1.85 (m, 2H), 1.95–2.10 (m, 4H), 2.15–2.23 (m, 5H), 3.00–3.13 (m, 2H), 3.93–4.00 (m, 1H), 5.12 (qt, J=6.5, 2.0 Hz, 1H), 5.93 (bs, 2H), 6.59 (s, 1H), 7.69 (s, 1H), 7.89 (d, J=6.0 Hz, 1H) m.p.; 144°–145° C.

EXAMPLE 14 endo-4-Amino-5-chloro-2-{(1-hexyn-3-yl)oxy}-
N-(8-methyl-8-azabicyclo[3.2.1]oct-3-yl)benzamide

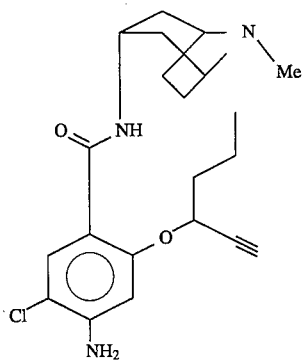

¹H-NMR (400 MHz, d₆-DMSO) δ ppm; 0.93 (t, J=7.5 Hz, 3H), 1.40–1.60 (m, 4H), 1.62–1.78 (m, 2H), 1.80–2.22 (m, 6H), 2.15 (s, 3H), 3.00 (bs, 2H), 3.70 (s, 1H), 3.90–4.00 (m, 1H), 4.98 (t, J=4.0 Hz, 1H), 5.94 (bs, 2H), 6.60 (s, 1H), 7.69 (s, 1H), 7.76 (d, J=6.0 Hz, 1H)

EXAMPLE 15 endo-4-Amino-5-chloro-2-(2-fluoroethoxy)-
N-(8-methyl-8-azabicyclo[3.2.1]oct-3-yl)benzamide

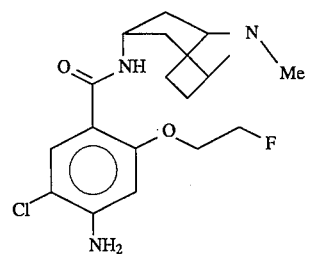

¹H-NMR (400 MHz, d₆-DMSO) δ ppm; 1.50–1.60 (m, 2H), 1.62–1.75 (m, 2H), 1.90–2.18 (m, 4H), 2.13 (s, 3H), 2.98–3.03 (m, 2H), 3.95–4.00 (m, 1H), 4.25–4.28 (m, 1H), 4.32–4.35 (m, 1H), 4.75–4.77 (m, 1H), 4.88–4.90 (m, 1H), 5.92 (bs, 2H), 6.55 (s, 1H), 7.68 (s, 1H), 7.77 (d, J=7.0 Hz, 1H)

EXAMPLE 16 endo-4-Amino-5-chloro-2-(3-cyanopropoxy)-
N-(8-methyl-8-azabicyclo[3.2.1]oct-3-yl)benzamide

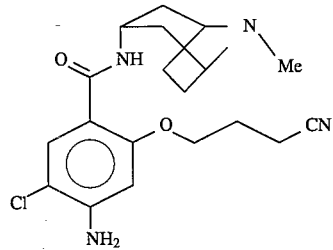

¹H-NMR (400 MHz, d₆-DMSO) δ ppm; 1.52–1.59 (m, 2H), 1.65–1.74 (m, 2H), 1.95–2.15 (m, 6H), 2.13 (s, 3H), 2.66 (t, J=7.0 Hz, 2H), 2.97–3.02 (m, 2H), 3.94–3.99 (m, 1H), 4.14 (t, J=6.0 Hz, 2H), 5.90 (bs, 2H), 6.50 (s, 1H), 7.66 (s, 1H), 7.80 (d, J=7.0 Hz, 1H)

EXAMPLE 17 endo-4-Amino-5-chloro-2-(1-cyclopentylethoxy)-
N-(8-methyl-8-azabicyclo[3.2.1]oct-3-yl)benzamide

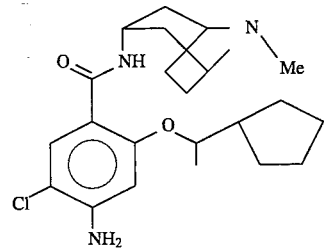

¹H-NMR (400 MHz, d₆-DMSO) δ ppm; 1.18–1.35 (m, 5H), 1.43–1.65 (m, 6H), 1.66–1.83 (m, 4H), 3.93–2.23 (m, 8H), 3.01–3.13 (m, 2H), 3.93–4.00 m, 1H), 4.22–4.31 (m, 1H), 5.84 (s, 2H), 6.56 (s, 1H), 7.70 (s, 1H), 7.96 (d, J=5.5 Hz, 1H)

EXAMPLE 18 endo-4-Amino-5-chloro-N-(8-methyl-
8azabicyclo[3.2.1]-oct-3-yl)-2-(tetrahydro-
4H-pyran-4-oxy)benzamide

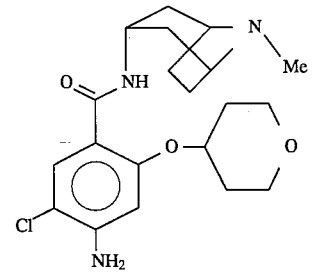

¹H-NMR (400 MHz, d₆-DMSO) δ ppm; 1.53–1.80 (m, 6H), 1.93–2.13 (m, 6H), 2.17 (s, 3H), 3.00–3.13 (m, 2H), 3.38–3.48 (m, 2H), 3.88–3.98 (m, 3H), 4.51–4.61 (m, 1H), 5.85 (bs, 2H), 6.62 (s, 1H), 7.68 (s, 1H), 7.85 (d, J=6.0 Hz, 1H)

EXAMPLE 19 endo-4-Amino-5-chloro-2-(4-methoxycyclohexyloxy)-N-(8-methyl-8-azabicyclo[3.2.1]oct-3-yl)benzamide

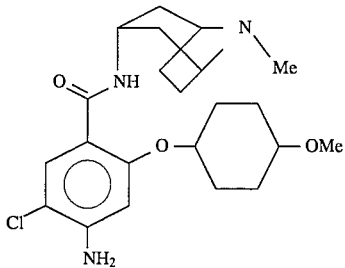

¹H -NMR (400 MHz, d₆-DMSO) δ ppm; 1.20–1.35 (m, 1H), 1.43–1.68 (m, 4H), 1.69–1.81 (m, 3H), 1.82–1.91 (m, 1H), 1.95–2.25 (m, 10H), 3.23 (s, 3H), 3.26–3.36 (m, 2H), 3.39–3.50 (m, 1H), 3.91–4.00 (m, 1H), 4.80–4.48 (m, 1H), 5.83 (bs, 2H), 6.57 (s, 1H), 7.68 (s, 1H), 7.85 (d, J=5.0 Hz, 1H)

EXAMPLES 20 TO 34

The following compounds were prepared in a similar manner to that of the Example 2.

EXAMPLE 20 endo-4-Amino-5-chloro-N-(8-methyl-8-azabicyclo[3.2.1]oct-3-yl)-2-{(1-pentyn-3-yl)oxy}benzamide hydrochloride

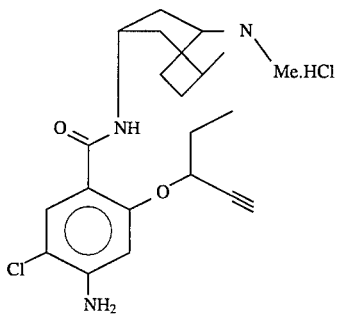

¹H-NMR (400 MHz, d₆-DMSO) δ ppm; 1.02 (t, J=8.0 Hz, 3H), 1.82–2.12 (m, 6H), 2.21–2.24 (m, 2H), 2.40–2.44 (m, 2H), 2.62 (d, J=6.0 Hz, 3H), 3.72 (s, 2H), 3.82 (bs, 2H), 3.93–4.03 (m, 1H), 4.93 (t, J=4.0 Hz, 1H), 6.62 (s, 1H), 7.60 (s, 1H), 7.86 (d, J=5.0 Hz, 1H) MS m/z (FAB); 376 (M⁺+1)

EXAMPLE 21 endo-4-Amino-5-chloro-(8-methyl-8-azabicyclo[3.2.1]oct-3-yl)-2-propargyloxybenzamide hydrochloride

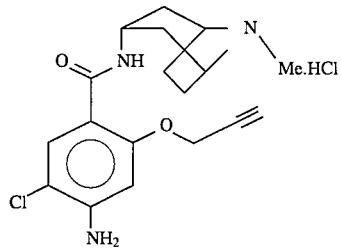

¹H-NMR (400 MHz, d₆-DMSO) δ ppm; 1.90–2.10 (m, 2H), 2.11–2.30 (m, 4H), 2.41–2.53 (m, 2H), 2.63 (s, 3H), 3.72 (t, J=2.0 Hz, 1H), 3.78–3.85 (m, 2H), 3.94–4.03 (m, 1H), 4.86 (d, J=2.0 Hz, 1H), 6.01 (bs, 2H), 6.53 (s, 1H), 7.62 (s, 1H), 8.00 (d, J=5.0 Hz, 1H) m.p.; 242°–245° C.

EXAMPLE 22 endo-4-Amino-2-(2-butynyloxy)-5-chloro-N-(8-methyl-8-azabicyclo[3.2.1]oct-3-yl)benzamide hydrochloride

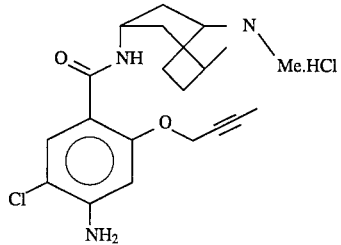

¹H-NMR (400 MHz, d₆-DMSO) δ ppm; 1.86 (bs, 3H), 2.00–2.06 (m, 2H), 2.15–2.31 (m, 4H), 2.36–2.45 (m, 2n), 2.65 (s, 3H), 3.80–3.88 (m, 2H), 3.96–4.04 (m, 1H), 4.8 (bs, 2H), 6.00 (bs, 2H), 6.50 (s, 1H), 7.63 (s, 1H), 8.05 (d, J=7.0 Hz, 1H) MS m/Z (FAB); 362 (M⁺+1) m.p.; 263°–265° C.

EXAMPLE 23 endo-4-Amino-5-chloro-N-(8-methyl-8-azabicyclo[3.2.1]oct-3-yl)-2-(3-pentynyloxy)benzamide hydrochloride

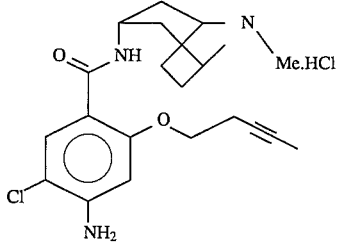

¹H-NMR (400 MHz, d₆-DMSO) δ ppm; 1.74 (t, 2.5 Hz, 3H), 2.06–2.15 (m, 2H), 2.20–2.30 (m, 4H), 2.38–2.46 (m, 2H), 2.64–2.73 (m, 5H), 3.80–3.93 (m, 2H), 3.95–4.03 (m, 1H), 4.10 (t, J=6.5 Hz, 2H), 6.51 (s, 1H), 7.65 (s, 1H), 7.93 (d, J=7.0 Hz, 1H) MS m/z (FAB); 376 (M⁺+1)

EXAMPLE 24 endo-4-Amino-2-{(3-butyn-2-yl)oxy}-5-chloro-N-(8-methyl-8-azabicyclo[3.2.1]oct-3-yl)benzamide hydrochloride

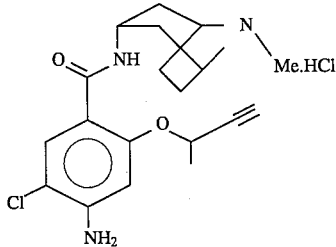

$^1$H-NMR (400 MHz, $d_6$-DMSO) δ ppm; 1.63 (d, J=6.5 Hz, 3H), 1.97–2.30 (m, 6H), 2.46–2.57 (m, 2H), 2.61 (d, J=5.0 Hz, 3H), 3.71 (d, J=3.0 Hz, 1H), 3.78–3.85 (m, 2H), 3.95–4.00 (m, 1H), 4.68 (bs, 2H), 5.12 (dq, J=3.0, 6.5 Hz, 1H), 6.62 (s, 1H), 7.61 (s, 1H), 7.88 (d, J=6.0 Hz, 1H) 10.68 (bs, 1H) MS m/z (FAB); 362 (M$^+$+1) m.p.; 154°–158° C.

EXAMPLE 25 endo-4-Amino-5-chloro-2-{(4-heptyn-3-yl)oxy}-N-(8-methyl-8-azabicyclo[3.2.1]oct-3-yl)benzamide hydrochloride

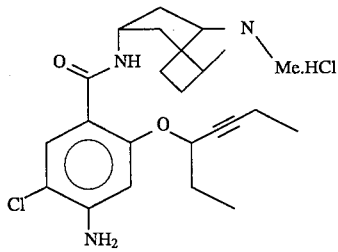

$^1$H-NMR (400 MHz, $d_6$-DMSO) δ ppm; 0.98–1.08 (m, 6H), 1.78–2.30 (m, 10H), 2.50–2.58 (m, 2H), 2.63 (d, J=5.0 Hz, 3H), 3.83 (bs, 2H), 3.93–4.00 (m, 1H), 4.90–4.96 (m, 1H), 6.63 (s, 1H), 7.64 (s, 1H), 7.94 (bs, 1H)

EXAMPLE 26 endo-4-Amino-5-chloro-2-{(4-heptyn-2-yl)oxy}-N-(8-methyl-8-azabicyclo[3.2.1]oct-3-yl)benzamide hydrochloride

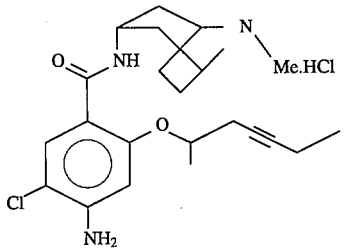

$^1$H-NMR (400 MHz, $d_6$-DMSO) δ ppm; 0.99 (t, J=7.5 Hz, 3H), 1.40 (d, J=4.0 Hz, 3H), 2.00–2.16 (m, 6H), 2.18–2.30 (m, 2H), 2.40–2.54 (m, 2H), 2.57–2.66 (m, 2H), 2.63 (d, J=5.0 Hz, 3H), 3.84 (bs, 2H), 3.94–3.99 (m, 1H), 4.53–4.62 (m, 1H), 6.56 (s, 1H), 7.66 (s, 1H), 7.92 (d, J=5.0 Hz, 1H), 10.40 (bs, 1H)

EXAMPLE 27 endo-4-Amino-5-chloro-2-{(2-hexyn-4-yl)oxy}-N-(8-methyl-8-azabicyclo[3.2.1]oct-3-yl)benzamide hydrochloride

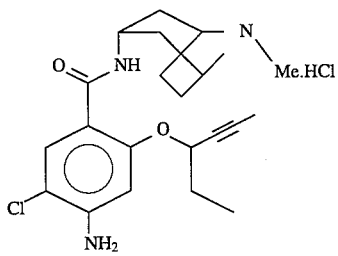

$^1$H-NMR (400 MHz, $d_6$-DMSO) δ ppm; 1.01 (t, J=7.5 Hz, 3H), 1.84 (d, J=2.0 Hz, 3H), 1.85–2.10 (m, 6H), 2.23–2.33 (m, 2H), 2.39–2.50 (m, 2H), 2.65 (d, J=6.0 Hz, 3H), 3.81–3.88 (m, 2H), 3.96–4.04 (m, 1H), 4.88–4.95 (m, 1H), 5.95 (bs, 2H), 6.61 (s, 1H), 7.63 (s, 1H), 7.92 (d, J=6.0 Hz, 1H) m.p.; 137°–141° C.

EXAMPLE 28 endo-4-Amino-5-chloro-2-{(3-hexyn-2-yl)oxy}-N-(8-methyl-8-azabicyclo[3.2.1]oct-3-yl)benzamide hydrochloride

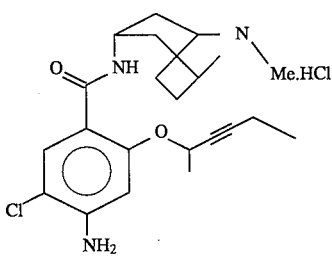

$^1$H-NMR (400 MHz, $d_6$-DMSO) δ ppm; 1.04 (t, J=7.5 Hz, 3H), 1.60 (d, J=6.5 Hz, 3H), 1.98–2.33 (m, 8H), 2.38–2.58 (m, 2H), 2.65 (d, J=5.0 Hz, 3H), 3.80–3.90 (m, 2H), 3.96–4.04 (m, 1H), 5.11 (qt, J=6.5, 2.0 Hz, 1H), 5.98 (bs, 2H), 6.61 (s, 1H), 7.64 (s, 1H), 7.94 (d, J=5.0 Hz, 1H) m.p.; 134°–136° C.

EXAMPLE 29 endo-4-Amino-5-chloro-2-{(1-hexyn-3-yl)oxy}-
N-(8-methyl-8-azabicyclo[3.2.1]oct-3-yl)benzamide
hydrochloride

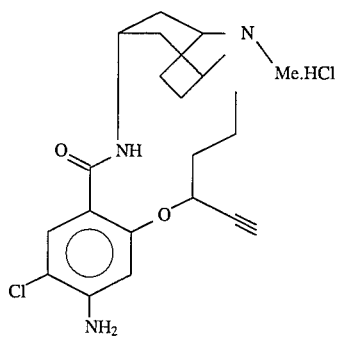

$^1$H-NMR (400 MHz, d$_6$-DMSO) δ ppm; 0.93 (t, J=7.5 Hz, 3H), 1.42–1.55 (m, 2H), 1.67–2.15 (m, 6H), 2.20–2.30 (m, 2H), 2.40–2.50 (m, 2H), 2.63 (d, J=5.0 Hz, 3H), 3.70 (s, 1H), 3.78–3.85 (m, 2H), 3.95–4.02 (m, 1H), 4.96 (t, J=4.0 Hz, 1H), 5.20 (bs, 2H), 6.62 (S, 1H), 7.60 (s, 1H), 7.82 (d, J=6.0 Hz, 1H) MS m/z (FAB); 390 (M$^+$+1) m.p.; 138°–140° C.

EXAMPLE 30 endo-4-Amino-5-chloro-2-(2-fluoroethoxy)-
N-(8-methyl-8-azabicyclo[3.2.1]oct-3-yl)benzamide
hydrochloride

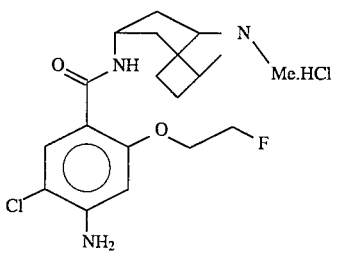

$^1$H-NMR (400 MHz, d$_6$-DMSO) δ ppm; 1.94–2.23 (m, 6H), 2.40–2.52 (m, 2H), 2.62 (bs, 3H), 3.72–3.85 (m, 2H), 3.94–4.04 (m, 1H), 4.26–4.29 (m, 1H), 4.33–4.37 (m, 1H), 4.74–4.78 (m, 1H), 4.87–4.90 (m; 1H), 6.04 (bs, 2H), 6.51 (s, 1H), 7.67 (s, 1H), 7.95 (d, J=7.0 Hz, 1H) m.p.; 260°–262° C.

EXAMPLE 31 endo-4-Amino-5-chloro-2-(3-cyanopropoxy)-
N-(8-methyl-8-azabicyclo[3.2.1]oct-3-yl)benzamide
hydrochloride

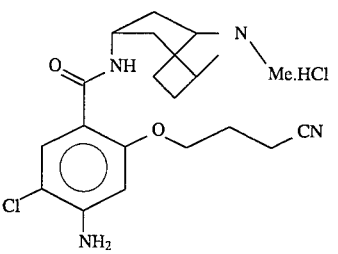

$^1$H-NMR (400 MHz, d$_6$-DMSO) δ ppm; 2.03–2.13 (m, 6H), 2.22–2.27 (m, 2H), 2.38–2.46 (m, 2H), 2.64 (d, J=5.4 Hz, 3H), 2.68 (t, J=7.5 Hz, 2H), 3.82 (m, 2H), 3.94–4.00 (m, 1H), 4.12 (t, J=6.8 Hz, 2H), 5.93 (bs, 2H), 6.52 (s, 1H), 7.56 (s, 1H), 7.88 (d, J=4.8 Hz, 1H), 10.14 (bs, 1H) MS m/z (FAB); 377 (M+H)$^+$ m.p.; 130°–132° C.

EXAMPLE 32 endo-4-Amino-5-chloro-2-(1-cyclopentylethoxy)-
N-(8-methyl-8-azabicyclo[3.2.1]oct-3-yl)benzamide
hydrochloride

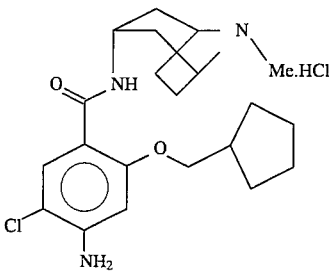

$^1$H-NMR (400 MHz, d$_6$-DMSO) δ ppm; 1.16–1.33 (m, 5H), 1.43–1.65 (m, 4H), 1.66–1.80 (m, 2H), 1.88–2.08 (m, 4H), 2.10–2.18 (m, 1H), 2.20–2.35 (m, 2H), 2.38–2.65 (m, 5H), 3.79–3.86 (m, 2H), 3.95–4.01 (m, 1H), 4.23–4.31 (m, 1H), 6.59 (s, 1H), 7.65 (s, 1H), 7.98 (d, J=5.0 Hz, 1H), 10.55 (br s, 1H) m.p.; 154°–156° C.

EXAMPLE 33 endo-4-Amino-5-chloro-N-(8-methyl-
8-azabicyclo[3.2.1]-oct-3-yl)-2-(tetrahydro-
4H-pyran-4-oxy)benzamide hydrochloride

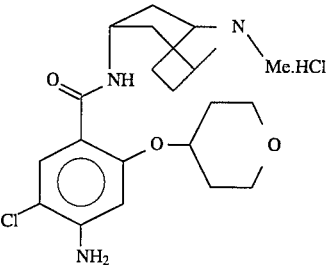

$^1$H-NMR (400 MHz, d$_6$-DMSO) δ ppm; 1.55–1.68 (m, 2H), 2.01–2.12 (m, 6H), 2.23–2.30 (m, 2H), 2.35–2.45 (m, 2H), 2.64 (d, J=5.0 Hz, 3H), 3.38–3.48 (m, 2J), 3.80–3.87 (m, 2H), 3.89–4.00 (m, 3H), 4.50–4.59 (m, 1H), 5.88 (bs, 2H), 6.63 (s, 1H), 7.61 (s, 1H), 7.90 (d, J=6.0 Hz, 1H) m.p.; 226°–228° C.

EXAMPLE 34 endo-4-Amino-5-chloro-2-(4-methoxycyclohexyloxy)-N-(8-methyl-8-azabicyclo[3.2.1]oct-3-yl)benzamide hydrochloride

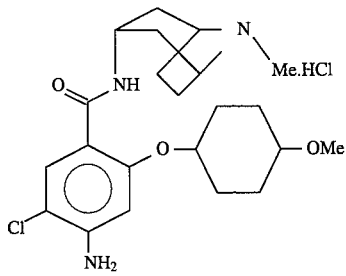

$^1$H-NMR (400 MHz, $d_6$-DMSO) δ ppm; 1.20–1.30 (m, 1H), 1.38–1.58 (m, 2H), 1.60–1.75 (m, 1H), 1.80–1.90 (m, 1H), 1.95–2.15 (m, 7H) 2.20–2.30 (m, 2H), 2.35–2.45 (m, 2H), 2.63 (s, 3H), 3.14–3.20 (m, 1H), 3.23 (s, 3H), 3.80–3.88 (m, 2H), 3.93–4.00 (m, 1H), 4.28 –4.40 (m, 1H), 5.88 (bs, 2H), 6.58 (s, 1H), 7.61 (s, 1H), 7.91 (d, J=5.0 Hz, 1H)

EXAMPLE 35

(−)-endo-4-Amino-5-chloro-N-(8-methyl-8-azabicyclo[3.2.1]oct-3-yl)-2-{(1-pentyn-3-yl)oxy}benzamide (+)-endo-4-Amino-5-chloro-N-(8-methyl-8-azabicyclo[3.2.1]oct-3-yl)-2-{(1-pentyn-3-yl)oxy}benzamide

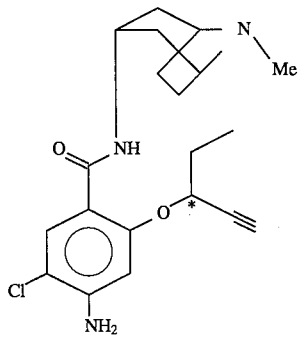

The title compounds were prepared in a similar manner to that of the Example 3.

(−)-isomer
m.p.: 179° to 182° C.
(+)-isomer
m.p.: 183° to 184° C.

EXAMPLES 36 TO 38

The following compounds were prepared in a similar manner to that of the Example 4.

EXAMPLE 36

(+)-endo-4-Amino-5-chloro-N-(8-methyl-8-azabicyclo[3.2.1]oct-3-yl)-2-{(3-pentyn-2-yl)oxy}benzamide hydrochloride

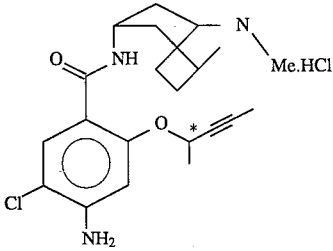

$^1$H -NMR (400 MHz, $d_6$-DMSO) δ ppm; 1.60 (d, J=6.5 Hz, 3H), 1.82 (d, J=2.0 Hz, 3H), 1.95–2.09 (m, 2H), 2.10–2.17 (m, 2H), 2.23–2.32 (m, 2H), 2.33–2.45 (m, 2H) 2.65 (d, J=5.0 Hz, 3H), 3.82–3.86 (m, 2H), 3.98–4.03 (m, 1H), 5.06–5.14 (m, 1H), 5.98 (bs, 2H), 6.60 (s, 1H), 7.63 (s, 1H), 7.92 (d, J=5.0 Hz, 1H) MS m/z (FAB); 376 (M$^+$+1) [α]$_D^{25}$=97.25° (c=1.09, MeOH)

EXAMPLE 37

(−)-endo-4-Amino-5-chloro-N-(8-methyl-8-azabicyclo[3.2.1]oct-3-yl)-2-{(1-pentyn-3-yl)oxy}benzamide hydrochloride

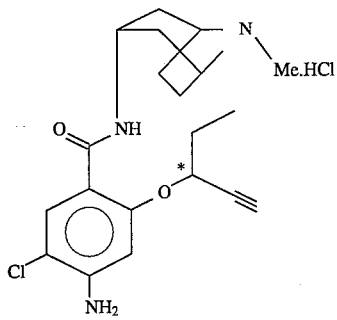

$^1$H-NMR (400 MHz, $d_6$-DMSO) δ ppm; 1.02 (t, J=8.0 Hz, 3H), 1.82–2.12 (m, 6H), 2.21–2.24 (m, 2H), 2.40–2.44 (m, 2H), 2.62 (d, J=6.0 Hz, 3H), 3.72 (s, 2H), 3.82 (bs, 2H), 3.93–4.03 (m, 1H), 4.93 (t, J=4.0 Hz, 1H), 6.62 (s, 1H), 7.60 (s, 1H), 7.86 (d, J=5.0 Hz, 1H) MS m/z (FAB); 376 (M$^+$+1) [α]$_D^{25}$=−74.55° (c=1.12, MeOH) m.p.; 144°–147° C.

EXAMPLE 38

(+)-endo-4-Amino-5-chloro-N-(8-methyl-8-azabicyclo[3.2.1]oct-3-yl)-2-{(1-pentyn-3-yl)oxy}benzamide hydrochloride

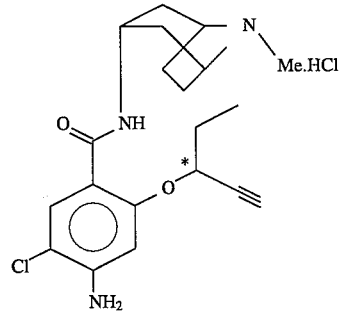

¹H-NMR (400 MHz, d₆-DMSO) δ ppm; 1.02 (t, J=8.0 Hz, 3H), 1.82–2.12 (m, 6H), 2.21–2.24 (m, 2H), 2.40–2.44 (m, 2H), 2.62 (d, J=6.0 Hz, 3H), 3.72 (s, 2H), 3.82 (bs, 2H), 3.93–4.03 (m, 1H), 4.93 (t, J=4.0 Hz, 1H), 6.62 (s, 1H), 7.60 (s, 1H), 7.86 (d, J=5.0 Hz, 1H) MS m/z (FAB); 376 (M¹+1) [α]_D²⁵=76.36° (c=1.10 MeOH) m.p.; 146°–148° C.

EXAMPLE 39 endo-4-Amino-5-chloro-N-(8-methyl-8-azabicyclo[3.2.1]oct-3-yl)-2-{(4-pentyn-2-yl)oxy}benzamide

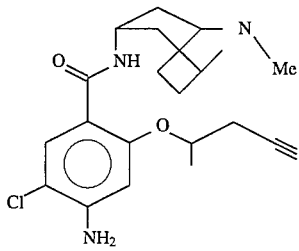

10 g of 4-amino-5-chloro-2-{(4-pentyn-2-yl)oxy}benzoic acid and 10 g of endo-3-amino-8-methyl-8-azabicyclo [3.2.1]octane were dissolved in 50 ml of pyridine, followed by the addition of 9.4 ml of a 5N aqueous solution of sodium hydroxide and 16.1 g of dicyclohexylcarbodiimide in this order. The obtained mixture was stirred at room temperature overnight, followed by the addition of water. Precipitated insolubles were filtered out and the obtained filtrate was made alkaline with a 5N aqueous solution of sodium hydroxide and extracted with chloroform. The organic phase was washed with a saturated aqueous solution of common salt, dried over anhydrous magnesium sulfate, and concentrated in a vacuum. The residue was purified by silica gel column chromatography (10% methanol/chloroform) to give 10.7 g of the title compound as a colorless crystal.

¹H-NMR (400 MHz, CDCl₃) δ ppm; 1.54 (d, J=6.0 Hz, 3H), 1.74–1.88 (m, 4H), 2.01–2.13 (m, 3H), 2.21–2.30 (m, 2H), 2.30 (s, 3H), 2.58 (A₂BX type, J=3.0, 7.0, 17.0 Hz, 1H), 2.68 (A₂BX type, J=3.0, 5.0, 17.0 Hz, 1H), 3.13–3.19 (m, 2H), 4.18–4.23 (m, 1H), 4.31–4.38 (bs, 2H), 4.60–4.69 (m, 1H), 6.32 (s, 1H), 7.89 (d, J=3.0 Hz, 1H), 8.10 (s, 1H) m.p.; 208°–209° C.

EXAMPLE 40 endo-4-Amino-5-chloro-N-(8-methyl-8-azabicyclo[3.2.1]oct-3-yl)-2-{(4-pentyn-2-yl)oxy}benzamide hydrochloride

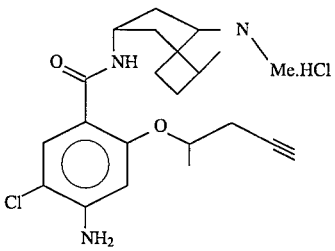

130 mg of endo-4-amino-5-chloro-N-(8-methyl-8-azabicyclo[3.2.1]oct-3-yl)-2-{(4-pentyn-2-yl)oxy}benzamide was dissolved in 2 ml of ethanol. The obtained solution was acidified by adding 20% hydrochloric acid/ethanol under cooling with ice, followed by the addition of diethyl ether. A crystal thus precipitated was recovered by filtration and dried to give 140 mg of the title compound as a colorless crystal.

¹H-NMR (400 MHz, d₆-DMSO) δ ppm; 1.41 (d, J=6.0 Hz, 3H), 2.03–2.14 (m, 4H), 2.21–2.29 (m, 2H), 2.40–2.53 (m, 2H), 2.60–2.68 (m, 5H), 3.01 (t, J=3.0 Hz, 1H), 3.80–3.85 (m, 2H), 3.98–4.00 (m, 1H), 4.60–4.66 (m, 1H), 6.57 (s, 1H), 7.67 (s, 1H), 7.86 (d, J=3.0 Hz, 1H) m.p.; 139°–141° C.

EXAMPLE 41

(+)-endo-4-Amino-5-chloro-N-(8-methyl-8-azabicylo[3.2.1]oct-3-yl)-2-{(4-pentyn-2-yl)oxy}benzamide (−)-endo-4-Amino-5-chloro-N-(8-methyl-8-azabicyclo[3.2.1]oct-3-yl)-2-{(4-pentyn-2-yl)oxy}benzamide

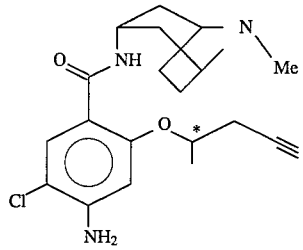

1.65 g of the racemic modification was subjected to high performance liquid chromatography using a chiral column (a product of Daicel Chemical Industries, Ltd.; CHIRALCEL OD) and a mobile phase solvent (ethanol:hexane:triethylamine=20:80:0.1) to give 480 mg of the (+)-isomer and 450 mg of the (−)-isomer.

(+)-isomer

¹H-NMR (400 MHz, CDCl₃) δ ppm; 1.54 (d, J=6.0 Hz, 3H), 1.71–1.88 (m, 4H), 2.01–2.13 (m, 3H), 2.21–2.30 (m, 2H), 2.30 (s, 3H), 2.58 (A₂BX type, J=3.0, 7.0, 17.0 Hz, 1H), 2.68 (A₂BX type, J=3.0, 5.0, 17.0 Hz, 1H), 3.13–3.19 (m, 2H), 4.18–4.23 (m, 1H), 4.35 (bs, 2H), 4.64 (tq, J=6.0, 6.0 Hz, 1H), 6.32 (s, 1H), 7.89 (d, J=5.5 Hz, 1H), 8.10 (s, 1H)

(−)-isomer

¹H-NMR (400 MHz, CDCl₃) δ ppm; 1.54 (d, J=6.0 Hz, 3H), 1.71–1.88 (m, 4H), 2.05–2.15 (m, 2H), 2.20–2.30 (m, 2H), 2.30 (s, 3H), 2.58 (A₂BX type J=3.0, 7.0, 17.0 Hz, 1H), 2.68 (A₂BX type, J=3.0, 5.0, 17.0 Hz, 1H), 3.13–3.19 (m, 2H), 4.15–4.24 (m, 1H), 4.33 (bs, 2H), 4.64 (tq, J=6.0, 6.0 Hz, 1H), 6.32 (s, 1H), 7.89 (d, J=5.5 Hz, 1H), 8.11 (s, 1H)

EXAMPLE 42

(+)-endo-4-Amino-5-chloro-N-(8-methyl-8-azabicyclo[3.2.1]oct-3-yl)-2-{(4-pentyn-2-yl)oxy}benzamide hydrochloride

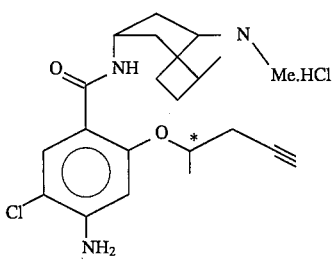

309 mg of (+)-endo-4-amino-5-chloro-N-(8-methyl-8-azabicyclo[3.2.1]oct-3-yl)-2-{(3-pentyn-2-yl)oxy}benzamide was dissolved in 1.5 ml of ethanol, followed by the addition of 0.411 ml of 2N hydrochloric acid and 15 ml of water in this order. The obtained mixture was freeze-dried to give 333 g of the (+)-isomer hydrochloride.

$^1$H-NMR (400 MHz, $d_6$-DMSO) δ ppm; 1.44 (d, J=6.5 Hz, 3H), 2.07–2.17 (m, 4H), 2.26–2.37 (m, 2H), 2.38–2.43 (m, 2H), 2.65–2.71 (m, 5H), 3.00 (t, J=2.5 Hz, 1H), 3.82–3.93 (m, 2H), 4.01–4.05 (m, 1H), 4.65 (tq, J=6.0, 6.0 Hz, 1H), 5.91 (bs, 2H), 6.59 (s, 1H), 7.69 (s, 1H), 7.88 (d, J=5.0 Hz, 1H), 9.87 (s, 1H) MS m/z (FAB); 376 (M$^+$+1)

EXAMPLE 43

(–)-endo-4-Amino-5-chloro-N-(8-methyl-8-azabicyclo[3.2.1]oct-3-yl)-2-{(4-pentyn-2-yl)oxy}benzamide hydrochloride

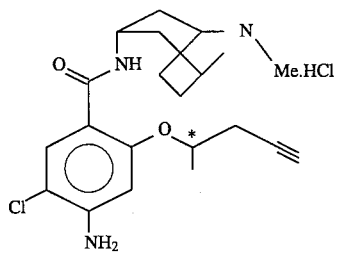

The title compound was prepared in a similar manner to that of the Example 42.

$^1$H-NMR (400 MHz, $d_6$-DMSO) δ ppm; 1.42 (d, J=6.0 Hz, 3H), 2.04–2.13 (m, 4H), 2.23–2.27 (m, 2H), 2.35–2.43 (m, 2H), 2.62–2.67 (m, 5H), 3.01 (t, J=3.0 Hz, 1H), 3.80–3.84 (m, 2H), 3.96–4.00 (m, 1H), 4.64 (tq, J=6.0, 6.0 Hz, 1H), 6.57 (s, 1H), 7.66 (s, 1H), 7.87 (d, J=5.0 Hz, 1H) MS m/z (FAB); 376 (M$^+$+1) $[α]_D^{25}$=–8.88° (c=1.07, MeOH)

EXAMPLE 44 endo-4-Acetamido-2-(3-butynyloxy)-5-chloro-N-(8-methyl-8-azabicyclo[3.2.1]oct-3-yl)benzamide

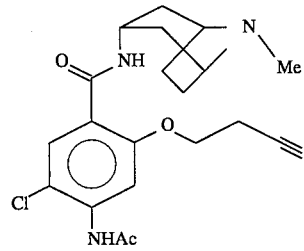

260 mg of 4-acetamido-2-(3-butynyloxy)-5-chlorobenzoic acid and 216 mg of endo-3-amino-8-methyl-8azabicyclo[3.2.1]octane were dissolved in 5 ml of pyridine, followed by the addition of 0.2 ml of a 5N aqueous solution of sodium hydroxide and 300 mg of 1,3-dicyclohexylcarbodiimide in this order. The obtained mixture was stirred at room temperature overnight, followed by the addition of water. Insolubles thus precipitated were filtered out and the filtrate was basified with an aqueous solution of sodium hydroxide and extracted with chloroform. The organic phase was washed with a saturated aqueous solution of common salt, dried over anhydrous magnesium sulfate, and concentrated in a vacuum. The residue was purified by silica gel column chromatography (10% methanol/chloroform) to give 130 mg of the title compound as a colorless crystal.

$^1$H-NMR (400 MHz, CDCl$_3$) δ ppm; 1.85–1.93 (m, 2H), 2.06 (t, J=3.0 Hz, 1H), 2.13–2.18 (m, 2H), 2.27 (s, 3H), 2.30–2.38 (m, 4H), 2.78 (dt, J=3.0, 7.0 Hz, 2H), 3.20–3.28 (m, 4H), 4.20–4.26 (m, 1H), 4.35 (t, J=7.0 Hz, 2H), 7.75–7.78 (m, 1H), 8.05–8.09 (m, 1H), 8.23 (s, 1H), 8.33 (s, 1H)

EXAMPLE 45 endo-4-Amino-2-(3-butynyloxy)-5-chloro-N-(8-methyl-8-azabicyclo[3.2.1]oct-3-yl)benzamide

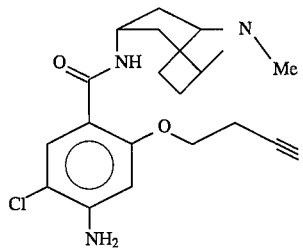

130 mg of endo-4-acetamido-2-(3-butynyloxy)-5-chloro-N-(8-methyl-8-azabicyclo[3.2.1]oct-3-yl)benzamide was dissolved in 5 ml of methanol, followed by the addition of a solution of 200 mg of sodium hydroxide in 1 ml of water. The obtained mixture was stirred at room temperature overnight. A crystal precipitated in the reaction system was recovered by filtration, washed with water and dried to give 120 mg of the title compound as a colorless crystal.

$^1$H-NMR (400 MHz, $d_6$-DMSO) δ ppm; 1.58–1.64 (m, 2H), 1.70–1.75 (m, 2H), 1.94–2.09 (m, 4H), 2.12 (s, 3H), 2.72 (dr, J=3.0, 7.0 Hz, 2H), 2.96–3.02 (m, 3H), 3.27–3.32 (m, 2H), 3.92–3.96 (m, 1H), 4.17 (t, J=7.0 Hz, 2H), 5.88–5.92 (m, 2H), 6.50 (s, 1H), 7.70 (s, 1H), 7.88 (d, J=7.0 Hz, 1H)

EXAMPLE 46 endo-4-Amino-2-(3-butynyloxy)-5-chloro-
N-(8-methyl-8-azabicyclo[3.2.1]oct-3-yl)benzamide
hydrochloride

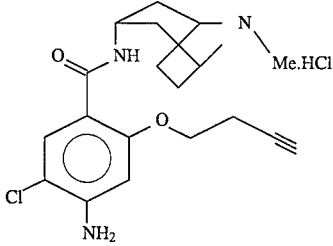

20 mg of endo-4-amino-2-(3-butynyloxy)-5-chloro-N-(8-methyl-8-azabicyclo[3.2.1]oct-3-yl)benzamide was dissolved in a mixture comprising 1 ml of ethanol and 7 ml of water, followed by the addition of 28 µl of a 2N aqueous solution of hydrochloric acid. The obtained mixture was freeze-dried to give 20 mg of the title compound as a colorless crystal.

$^1$H-NMR (400 MHz, d$_6$-DMSO) δ ppm; 2.06–2.15 (m, 4H), 2.23–2.30 (m, 2H), 2.31–2.40 (m, 2H), 2.65 (s, 3H), 2.69 (dt, J=3.0, 7.0 Hz, 2H), 3.01 (t, J=3.0 Hz, 1H), 3.81–3.86 (m, 2H), 3.96–4.01 (m, 1H), 4.15 (t, J=7.0 Hz, 2H), 6.51 (s, 1H), 7.65 (s, 1H), 7.91 (d, J=7.0 Hz, 1H) MS m/z (FAB); 362 (M$^+$+1) m.p.; 226°–229° C.

EXAMPLE 47

(S)-endo-4-Amino-5-chloro-N-(8,8-dimethyl-
8-azonia-bicyclo[3.2.1]oct-3-yl)-
2-{(3-pentyn-2-yl)oxy}-benzamide iodide

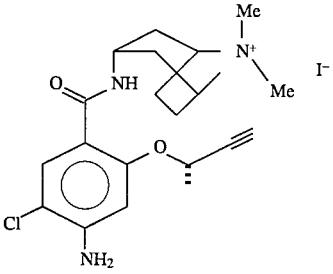

300 mg of (S)-(−)-endo-4-amino-5-chloro-N-(8-methyl-8-azabicyclo[3.2.1]oct-3-yl)-2-{(3-pentyn-2-yl)oxy}-benzamide was dissolved in 2 ml of ethanol, followed by the addition of 0.1 ml of methyl iodide at room temperature. After stirring the obtained solution for four hours, a crystal precipitated was recovered by filtration, washed twice with a small amount of cool ethanol and dried to give 257 mg of the title compound as a white crystal.

$^1$H-NMR(400 MHz, d$_6$-DMSO) δ ppm; 1.59–1.60 (d, 3H), 1.82–1.83 (d, 3H), 1.90–1.96 (m, 2H), 2.16–2.20 (d, 2H), 2.38–2.42 (m, 2H), 2.50–2.59 (m, 2H), 3.01 (s, 3H), 3.12 (s, 3H 3.84 (br.s, 2H), 4.10–4.16 (dd, 1H), 5.03–5.11 (m, 1H), 5.99 (s, 2H), 6.60 (s, 1H), 7.62 (s, 1H), 7.92–7.95 (d, 1H) MS m/z (FAB ); 390 (M$^+$) m.p.; 195° C.(dec.)

EXAMPLE 48

(S)-endo-4-amino-5-chloro-N-(8-methyl-
8-azabicyclo[3.2.1]oct-3-yl)-
2-{(3-pentyn-2-yl)oxy}benzamide 8-oxide

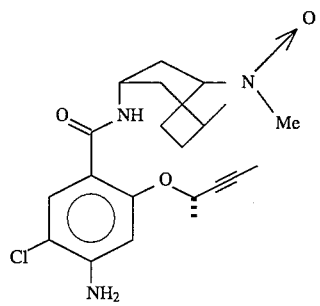

1.13 g of (S)-endo-4-amino-5-chloro-N-(8-methyl-8-azabicyclo[3.2.1]oct-3-yl)-2-{(3-pentyn-2-yl)oxy}benzamide was dissolved in 50 ml of dichloromethane, followed by the addition of 0.81 g of m-chloroperbenzoic acid under cooling with ice. The obtained solution was stirred for a half hour. After completing the reaction, the reaction mixture thus obtained was washed with a saturated aqueous solution of sodium hydrogencarbonate and a saturated aqueous solution of common salt in this order, dried over magnesium sulfate. After the solvent was evaporated, the residue was treated with diisopropylether to give 0.40 g of the title compound.

$^1$H-NMR (400 MHz, CDCl$_3$) δ ppm; 1.65, 1.67 (2×d, J=6.5 Hz, 3H), 1.83, 1.84 (2×d, J=1.5 Hz, 3H), 1.90–2.40 (m, 6H), 2.47–2.57 (m, 1H), 2.79–2.86 (m, 1H), 3.27, 3.30 (s×2, 3H), 3.43, 3.66 (2×m, 2H), 4.30 (m, 1H), 4.41, 4.45 (2×br.s, 2H), 4.88 (m, 1H), 6.42, 6.43 (s×2, 1H), 8.08, 8.10 (2×s, 1H), 8.00, 8.14 (2×br.d, J=5.5 Hz, 1H) MS m/z (FAB); 392 (M$^+$+1)

EXAMPLE 49

(S)-exo-4-amino-5-chloro-N-(8-methyl-
8-azabicyclo[3.2.1]oct-3-yl)-
2-{(3-pentyn-2yl)oxy}benzamide

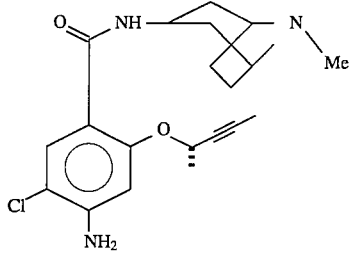

The title compound was prepared from exo-3-aminotropane and (S)-4-amino-5-chloro-2-{(3-pentyn-2-yl)oxy}benzoic acid in a similar manner to that of the Example 1.

$^1$H-NMR (400 MHz, CDCl$_3$) δ ppm; 1.68 (d, J=6.5 Hz, 3H), 1.83 (d, J=2.0 Hz, 3H), 1.73–1.88 (m, 4H), 1.92–2.02 (m, 2H), 2.05–2.14 (m, 2H), 2.38 (s, 3H), 3.32 (m, 2H), 4.32 (m, 1H), 4.42 (br.s, 2H), 4.75–4.83 (m, 1H), 6.48 (s, 1H), 7.64 (br.d, J=5.0 Hz, 1H), 8.01 (s, 1H) MS m/z (FAB); 376 (M$^+$+1)

EXAMPLE 50

(S)-exo-4-amino-5-chloro-N-(8-methyl-8-azabicyclo[3.2.1]oct-3-yl)-2-{(3-pentyn-2yl)oxy}benzamide hydrochloride

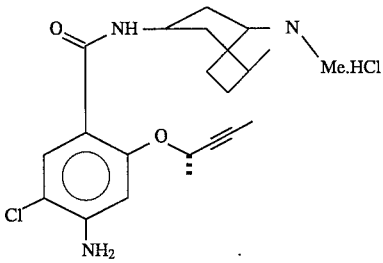

The title compound was prepared in a similar manner to that of the Example 2.

$^1$H-NMR (400 MHz, $d_6$-DMSO) δ ppm; 1.63 (d, J=6.5 Hz, 3H), 1.81 (d, J=1.5 Hz, 3H), 1.88–2.25 (m, 8H), 2.61 (d, J=6.0 Hz, 3H), 3.85 (m, 2H), 4.21 (m, 1H), 4.98 (m, 1H), 6.59 (s, 1H), 7.64 (d, J=5.5 Hz, 1H), 7.65 (s, 1H), 10.94 (br.s, 1H) MS m/z (FAB); 376 ($M^+$+1)

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. An aminobenzoic acid derivative represented by the following formulas (I-2) or (I-3), or a pharmacologically acceptable salt thereof;

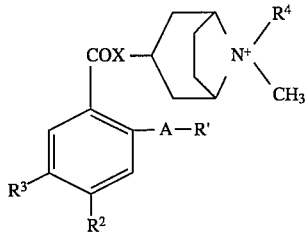

wherein $R^1$ represents a tetrahydrofuranyl or a 1,3-benzodioxolanyl group;

$R^2$ represents an amino, a monoacyl or diacylamino, —NHCOOH or a mono- or di-substituted alkylamino group;

$R^3$ represents a halogen atom;

X represents a group represented by the formulas: —O— or —NH—;

A represents an oxygen or sulfur atom; and $R^4$ represents a $C_1$–$C_8$ lower alkyl or aralkyl group wherein said alkyl moiety has 1 to 8 carbon atoms, and

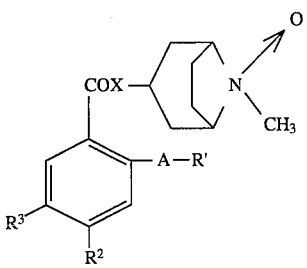

wherein $R^1$ represents a tetrahydrofuranyl group or a 1,3-benzodioxolanyl group;

$R^2$ represents an amino, a mono- or di-acylamino, —NHCOOH or a mono- or di-substituted alkylamino group;

$R^3$ represents a halogen atom;

X represents a group represented by the formulas: —O— or —NH—; and

A represents an oxygen or sulfur atom.

2. The aminobenzoic acid derivative or a pharmacologically acceptable salt thereof as set forth in claim 1, wherein $R^2$ is an amino group.

3. A pharmacological composition which comprises a therapeutically effective amount of the aminobenzoic acid derivative or the pharmacologically acceptable salt thereof as set forth in claim 1 and a pharmacologically acceptable vehicle.

4. A method of treating a disease caused by excess serotonin which comprises administering a pharmaceutically effective amount of the aminobenzoic acid derivative or the pharmacologically acceptable salt thereof as set forth in claim 1 to a patient suffering from said disease.

5. A method for treating a disease caused by acetyl choline deficiency which comprises administering a pharmaceutically effective amount of the aminobenzoic acid derivative or the pharmacologically acceptable salt thereof as set forth in claim 1 to a patient suffering from said disease.

6. The aminobenzoic acid derivative or a pharmacologically acceptable salt thereof as set forth in claim 1, wherein the aminobenzoic acid derivative is one member selected from the group consisting of compounds represented by the formulas (I-2) and (I-3).

7. A method for accelerating the release of acetylcholine in a host which comprises administering to a host in need thereof, a pharmacologically effective amount of an aminobenzoic acid derivative according to claim 1, or a pharmacologically acceptable salt thereof.

8. A method of treating anxiety which comprises administering to a patient in need of such treatment, a therapeutically acceptable amount of an aminobenzoic acid derivative according to claim 1, or a pharmacologically acceptable salt thereof.

9. A method of treating irritable bowel syndrome which comprises administering to a patient in need of such treatment, a therapeutically acceptable amount of an aminobenzoic acid according to claim 1, or a pharmacologically acceptable salt thereof.

10. A method of treating emesis which comprises administering to a patient in need of such treatment, a therapeutically acceptable amount of an aminobenzoic acid according to claim 1, or a pharmacologically acceptable salt thereof.

11. A method of treating amnestic syndrome, senile dementia, Alzheimer's disease, or dependencies, which comprises administering to a patient in need of such treatment, a therapeutically acceptable amount of an aminobenzoic acid according to claim 1, or a pharmacologically acceptable salt thereof.

12. A method of inhibiting the release of serotonin in a host which comprises administering to a host in need thereof, a therapeutically effective amount of aminobenzoic acid derivative according to claim 1, or a pharmacologically acceptable salt thereof.

* * * * *